United States Patent [19]

Nagano et al.

[11] Patent Number: 6,081,579

[45] Date of Patent: Jun. 27, 2000

[54] STRUCTURAL PARAMETER ANALYZING APPARATUS AND ANALYZING METHOD

[75] Inventors: Ichiro Nagano; Yuichiro Murakami, both of Yokohama, Japan

[73] Assignee: Mitsubishi Heavy Industries, Ltd., Tokyo, Japan

[21] Appl. No.: 08/813,202

[22] Filed: Mar. 7, 1997

[30] Foreign Application Priority Data

Mar. 8, 1996 [JP] Japan .................................. 8-051448
Oct. 31, 1996 [JP] Japan .................................. 8-289779

[51] Int. Cl.$^7$ .................................................. G01N 23/207
[52] U.S. Cl. .................................................. 378/73; 378/54
[58] Field of Search .................................. 378/73, 74, 75, 378/76, 77, 78, 54

[56] References Cited

U.S. PATENT DOCUMENTS 5,483,960  1/1996  Steiger et al. ........................ 128/653.1

FOREIGN PATENT DOCUMENTS

0603943A1  6/1994  European Pat. Off. .

OTHER PUBLICATIONS

J. Nguyen et al., "A Computer Program to Analyze X–Ray Diffraction Films," Review of Scientific Instruments, vol. 64, No. 12, Dec. 1993, pp. 3456–3461.

E.H. Kisi, "Rietveld Analysis of Powder Diffraction Patterns," Materials Forum, vol. 18, 1994, pp. 135–153.

The Rietveld Method, Fujio Izumi: Journal of the Crystallography Society of Japan 34, 76 (1992).

Primary Examiner—David V. Bruce

[57] ABSTRACT

In a crystal structure analysis using an X-ray diffraction method or the like, using a measured value $y°i$ of a sample and an expected crystal structure parameter, a vector F having the logarithmic conversion value of the measured value as a matrix element is determined by $f_i = k \cdot \log(y_i + \delta - b_i)$ from a value $y_i$ of the measured value $y°i$ after count missing correction of a detector, a background strength $b_i$ and a positive value $\delta$ of less than 1, a vector $F_c$ having the logarithmic conversion value of the calculated value as a matrix element is obtained by $F_{ci} = k \cdot \log(y_{ci})$ from the value vector obtained by calculation from the crystal structure parameter, a weight matrix W is obtained from device function matrix, systematic error, and accidental error, and the calculated value vector $F_c$ is determined so that a residual square sum s $(=(F-F_c)^t W(F-F_c))$ obtained by multiplying a difference between F and $F_c$ by the weight matrix is minimized and converged to obtain a crystal structure parameter.

64 Claims, 9 Drawing Sheets

PROFILE FITTING WHEN DEVICE FUNCTION IS NOT CONSIDERED
(ENLARGED IN THE DIRECTION OF AXIS OF ABSCISSAS)

PROFILE FITTING WHEN DEVICE FUNCTION IS CONSIDERED
(ENLARGED IN THE DIRECTION OF AXIS OF ABSCISSAS)

STRUCTURAL PARAMETER ANALYZING APPARATUS AND ANALYZING METHOD

FIELD OF THE INVENTION

This invention relates to a structural parameter analyzing apparatus and analyzing method, which is useful in research and development of various functional crystalline materials such as ceramics, metal materials, organic materials, and the like, and which can be widely applied in crystal structure analyzing for all crystalline materials, whether polycrystal samples or single crystal samples, to obtain favorable effects. The present invention can also be applied to vibration analysis by Raman spectroscopy, surface state analysis by electron diffraction, band state analysis by photoluminescence method and the like to obtain good effects as well.

DESCRIPTION OF THE PRIOR ART

As a crystal structure analyzing method for polycrystal materials, the Rietveld method has been known. However, in the Rietveld crystal structure analysis by practical X-ray diffraction, it is difficult to analyze light elements (such as anions) and heavy elements simultaneously because light elements are weak in diffraction strength. As such, information of light elements could not be obtained if applied to metal oxides or ceramics containing light and heavy elements. Therefore, a neutron source such as a nuclear reactor has been constructed to obtain information of light elements by the Rietveld crystal structure analysis method using a neutron diffraction method. Construction of the neutron source, however, has required an enormous cost. The above are problems in the spectrum strength axis (axis of ordinates or y-axis) direction.

On the other hand, regarding the resolution in the angular axis (axis of abscissas or x-axis) direction, since an ordinary counter-cathode type X-ray source is wide in wavelength width and has a doublet, a high-resolution result cannot be obtained unless a synchrotron orbital radiation (hereinafter referred to as SOR) is used. This has required an enormous cost for construction of an accelerator as in the above-described nuclear reactor.

The Rietveld crystal structure analysis method (hereinafter referred to as Rietveld method) will now be briefly described. In the Rietveld method, using equations of $s=\Sigma w_i(y_i-y_{ci})^2$ and $w_i=1/y_i$, a crystal structure parameter to minimize s is obtained by a nonlinear least square method, wherein $y_i$ is a measured value (called an observation value or count value) of diffraction strength, $y_{ci}$ is a calculation value, $w_i$ is a statistical weight, suffix i is a number of a measuring point, and s is a residual square sum. The calculation value $y_{ci}$ is obtained by calculating from a crystal structure parameter previously expected for the sample, a crystal structure parameter which minimizes s, obtained by repeating calculation of $y_{ci}$ by successively changing the crystal structure parameter from its initial value so that s becomes a minimum, which is determined to be the crystal structure analytical result of the sample.

As can be seen from these formulae, the Rietveld method considers only-statistical variations (called accidental errors, white noise, quantum noise, or Poisson distribution), but does not consider systematic errors. Further, to extract all of information included in the data by the least square method, it is considered to be optimal that the relation of $w_i$ $1/\sigma i^2$ ($\sigma i^2$ is a variance at measuring point i) to the measured value and calculated value of weight $w_i$ appearing in the normal equation, or more strictly, to be set to $W \Sigma^{-1}$ as a weight matrix W including a non-diagonal term. However, this principle is not observed in the Rietveld method in spite of the fact that a systematic error exceeding the statistical variation is present in the covariation matrix, but omitted in the weight matrix to be an inverse matrix has been a problem.

Therefore, these problems become significant for longer measuring times or for weaker diffraction lines, which make it difficult to achieve analysis of light elements or trace ingredients and analysis with high resolution.

To obtain information of light elements in heavy elements by a practical X-ray diffraction method, it is necessary to improve the Rietveld crystal structure analysis method to achieve higher precision in order to extract as much information of light elements contained slightly in the diffraction spectrum as possible.

Further, to obtain high resolution from a low-resolution X-ray diffraction method, it is necessary to actually measure a spread of diffraction lines due to the measuring device (hereinafter referred to as device function) and to make substantial inverse calculations.

In general, to extract all of the information included in the data by the least square method, it is said to be the best that, as shown above, weight $w_i$ appearing in the normal equation is set to Formula 1 ($w_i$ is proportional to $1/\delta_i^2$ is equal to $<1/(y_i-y_{ci})^2>$, wherein the value in < > shows an expectation value, to the measured value $y_i$ and calculated $y_{ci}$, or more strictly, the weight matrix W is set to Formula 2 to the measured value vector F and calculated value vector $F_c$. To correctly set the weight matrix W, it is most important to exactly evaluate a difference between the measured value and the calculated value, that is, the cause of the error.

$$w_i \ 1/\sigma_i^2 = <1/(y_i-y_{ci})^2> \quad (1)$$

wherein the value in < > indicates an expectation value.

$$W \Sigma^{-1} = <(F-F_c)^t(F-F_c)> \quad (2)$$

wherein W is a weight matrix, $\Sigma$ is a covariation matrix,

F is a vector having $f_i=k\cdot\log(y_i+\delta-b_i)$ as a matrix element, $F_c$ is a vector having $f_{ci}=k\cdot\log(y_{ci})$ as a matrix element, $y_i$ is a i'th measured value after count missing correction, and k is an optional constant, i is a number of measuring point, $\delta$ is a positive number of less than 1, $b_i$ is an i'th background strength, the value in < > is an expectation value, and the right side $^t$ indicates a transposition matrix.

However, as described above, the Rietveld method is a method for analyzing the crystal structure using a nonlinear least square method, which only considers the statistical variation but cannot analyze the magnitude of error in detail. This is the reason that the prior art Rietveld method cannot provide a sufficient result for light elements.

Further, in spite of the fact that information of spread due to the measuring device itself is often included in the spectrum, this information is not utilized, and the resolution cannot be enhanced.

Therefore, a primary object of the present invention is to provide a structural parameter analyzing apparatus and analyzing method which, not limited to the Rietveld crystal structure analyzing method nor to polycrytalline samples, can analyze various crystal structures with high resolution, and can be applied to vibration analysis by Raman spectroscopy, surface state analysis by electron diffraction method, band state analysis by photoluminescence method and the like.

SUMMARY OF THE INVENTION

In accordance with the present invention, there is provided a structural parameter analyzing apparatus which includes a structural parameter setting unit for previously setting a structural parameter, a data input unit for inputting a measured value of a sample, calculation value calculating means for determining a calculation value corresponding to the measured value according to the structural parameter from the structural parameter setting unit, first logarithmic conversion means for making logarithmic conversion of the calculation value, second logarithmic conversion means for logarithmic converting a value of the measured value subtracted by a background strength, sum total calculation means for squaring a difference between the two logarithmic conversion values obtained by the first and second logarithmic conversion means to obtain a sum total s, a determination unit for determining a minimum of a plurality of sum totals obtained by the sum total calculation means by varying the structural parameter, and an output unit for outputting a structural parameter to be a minimum sum total s.

In the structural parameter analyzing apparatus according to another aspect of the invention, the second logarithmic conversion means subtracts the background strength from the measured value, adds a positive number of less than 1, and further makes logarithmic conversion.

The structural parameter analyzing apparatus according to another aspect of the invention further includes weight calculation means for obtaining a weight $w_i$ Formula 3 from the two logarithmic conversion values obtained by the first and second logarithmic conversion means, the sum total calculation means using Formula 3 squares a difference between the two logarithmic conversion values obtained by the first and second logarithmic conversion means and multiplies with the weight $w_i$ obtained by the weight calculation means to obtain a sum total.

$$S = \sum_{i=1}^{n} W_i \{k \cdot \log(y_i + \delta - b_i) - k \cdot \log(y_{ci})\}^2 \tag{3}$$

$$W_i = \left\langle 1 + \left\{ (n-m) \cdot k^2 (y_i + \delta - b_i)^{-2} (y_i + \delta) - (n-m)/n \cdot \right.\right.$$

$$\left.\left. \sum_{j=1}^{n} k^2 (y_j + \delta - b_j)^{-2} (y_j + \delta) \right\} \right/$$

$$\left. \sum_{j=1}^{n} \{k \cdot \log(y_j + \delta - b_j) - k \cdot \log(y_{cj})\}^2 \right\rangle^{-1} n^{-1}$$

wherein i and j are numbers of measuring points, n is a total number of measuring points, m is a number of independent variables, k is an optional constant, $w_i$ is a weight, $y_I$ and $y_j$ are measured values, $\delta$ is a positive number of less than 1, $b_I$ and $b_j$ are background strengths, and $y_{cI}$ are calculated values.

The structural parameter analyzing apparatus according to another aspect of the invention includes weight calculation means for obtaining a weight matrix W by Formula 4 from vectors F and $F_c$ using two logarithmic conversion values obtained by the first and second logarithmic conversion means as matrix elements, wherein the sum total calculation means using Formula 4 multiplies a transposition matrix $(F-F_c)^t$ a difference between two logarithmic conversion value vectors obtained by the first and second logarithmic conversion means, by the weight matrix W obtained by the weight calculation means, and by a difference $(F-F_c)$ between two logarithmic conversion values obtained by the first and second logarithmic conversion means to obtain a sum total s.

$$S = (F - F_c)^t W (F - F_c) \tag{4}$$

$$W = \left( \sum_{POI} + \sum_{SYS} \right)^{-t}$$

$$\sum_{SYS} = \langle (F - F_c)^t (F - F_c) - (n-m)/n \cdot$$

$$\sum_{j=1}^{n} \{k^2 (y_j + \delta - b_j)^{-2} (y_j + \delta)\} \rangle / n \cdot H^t H$$

wherein s is a residual square sum, i and j are numbers of measuring points, $y_i$ is an i'th measured value after count missing correction, $y_{ci}$ is an i'th calculated value, k is an optional constant, n is a number of total measuring points, m is a number of independent variables, $\delta$ is a positive number of less than 1, $b_i$ is an i'th background strength, W is a weight matrix of n lines and n lows, F is a vector of n lines and 1 row having $f_i = k \cdot \log(y_i + \delta - b_i)$ as a matrix element, $F_c$ is a vector of n lines and 1 row having $f_{ci} = k \cdot \log(y_{ci})$ as a matrix element, $\Sigma_{POI}$ is a covariation matrix of n lines and n rows having $k^2(y_i+\delta-b_i)^{-2} (y_i+\delta)$ as a diagonal element due to white noise (Poisson distribution), $\Sigma_{SYS}$ is a covariation matrix of n lines and n rows due to systematic error, H is a device function matrix (spread function matrix due to measuring device) of n lines and n rows, and $H^t$ is a transposition matrix of H.

In the structural parameter analyzing apparatus according to another aspect of the invention, the weight calculation means does not assume data measured r times under the same condition and Poisson distribution $(y_i + \frac{1}{2})$, uses a variance $\delta_{ir}-1^2$ obtained by measuring at each measuring point (point i), to obtain the weighting $w_i$ Formula 5 instead of Formula 3.

$$r\delta_{ir-1}^2 = \left\{ \sum_{j=1}^{r} (y_i(j) - y_i/r)^2 \right\} / (r-1) x r \tag{5}$$

$$y_i = \sum_{j=1}^{r} y_i(j)$$

$$s = \sum_{i=l}^{n} w_i \{k \cdot \log(y_i + \delta - b_i) - k \cdot \log(y_{ci})\}^2$$

$$w_i = \left\langle 1 + \left\{ (n-m) \cdot k^2 (y_i + \delta - b_i)^{-2} (r\delta_{ir-1}^2) - \right.\right.$$

$$\left.\left. (n-m)/n \cdot \sum_{j=1}^{n} k^2 (y_j + \delta - b_j)^{-2} (r\delta_{jr-l}^2) \right\} \right/$$

$$\left. \sum_{j=1}^{n} \{k \cdot \log(y_j + \delta - b_j) - k \cdot \log(y_{cj})\}^2 \right\rangle^{-1} n^{-1}$$

wherein $y_i(r)$ is an r'th measured value after count missing correction at point i, $y_i$ is a sum of measured values after count missing correction of r times at point i, i and j are numbers of measuring points, n is a total number of measuring points, m is a number of independent variables, k is an optional constant, $w_i$ is a weight, δ is a positive number of less than 1, $b_i$ and $b_j$ are background strengths, $y_{ci}$ and $y_{cj}$ are calculated values.

In a structural parameter analyzing apparatus according to another aspect of the invention, the weight calculation means does not assume data measured r times under the same condition and Poisson distribution ($y_i+\frac{1}{2}$), uses a variance $\delta_{ir-1}^2$ obtained by measuring at each measuring point (point i), to obtain the weight matrix W by Formula 6 instead of Formula 4.

$$r\delta_{ir-1}^2 = \left\{\sum_{j=1}^{r}(y_i(j) - y_i/r^2)\right\} / (r-l)x_r \quad (6)$$

$$y_i = \sum_{j=1}^{r} y_i(j)$$

$$s = (F - F_c)^t W(F - F_c)$$

$$W = \left(\sum_{POI} + \sum_{SYS}\right)^{-1}$$

$$\sum_{SYS} = \left\{(F - F_c)^t(F - F_c) - (n-m)/n \cdot \sum_{j=1}^{n}\{k^2(y_j + \delta - b_j)^{-2}(r\delta_{jr-l}^2)\}\right\} / n \cdot H^t H$$

wherein yi(r) is an r'th measured value after count missing correction at point i, $y_i$ is a sum of measured values after count missing correction of r times at point i, s is a residual square sum, i and j are numbers of measuring points, $y_{ci}$ an i'th calculated value, k is an optional constant, n is a total number of measuring points, m is a number of independent variables, δ is a positive number of less than 1, $b_i$ is an i'th background strength, W is a weight matrix of n lines and n rows, F is a vector of n lines and 1 row having $f_i=k\cdot\log(y_i+\delta-b_i)$ as a matrix element, $F_c$ is a vector of n lines and 1 row having $k\cdot\log(y_{ci})$ as a matrix element, $\Sigma_{POI}$ is a covariation matrix of n lines and n rows having $(y_i+\delta-b_i)^{-2}$ ($r\sigma_{ir-1}^2$) as a diagonal element due to white noise (Poisson distribution), ΣSYS is a covariation matrix of n lines and n rows due to systematic error, H is a device function matrix (spread function matrix due to measuring device) of n lines and n rows, H' is a transposition matrix of H.

A structural parameter analyzing apparatus according to another aspect of the invention further includes correction means for correcting for count missing of a detector for obtaining the measured value, wherein the second logarithmic conversion means makes logarithmic conversion of a value of the measured value after count missing correction subtracted by the background strength.

A structural parameter analyzing apparatus according to another aspect of the invention includes correction means for correcting for count missing of the detector for obtaining the measured value, wherein the second logarithmic conversion means makes logarithmic conversion of a value of the measured value after count missing correction subtracted by the background strength and after addition of a positive number of less than 1.

In a structural parameter analyzing apparatus according to another aspect of the invention, the number m of independent variables in Formula 3 to Formula 6 is set to zero, or omitted from the formulae.

Also disclosed is a structural parameter analyzing method for determining a structure of a sample by using a measured value of the sample and an expected structural parameter, including:

determining a calculated value corresponding to the measured value according to the expected structural parameter, and obtaining a first logarithmic conversion value by logarithmic conversion of the calculated value;

obtaining a second logarithmic conversion value by logarithmic conversion of the measured value subtracted by a background strength; and changing the structural parameter until the first and second logarithmic conversion values are sufficiently close to each other, determining the structural parameter at the close logarithmic conversion values to be an analytical result.

A structural parameter analyzing method according to another aspect of the invention is characterized in that the second logarithmic conversion value is determined by subtracting the background strength from the measured value, adding a positive number of less than 1, and making logarithmic conversion.

Also disclosed is a structural parameter analyzing method for determining a structure of a sample by using a measured value of the sample and an expected structural parameter, including:

determining a calculated value corresponding to the measured value according to the expected structural parameter, and obtaining a first logarithmic conversion value by logarithmic conversion of the calculated value;

making count missing correction to the measured value, subtracting the background strength from the corrected measured value, adding a positive number of less than 1, and making logarithmic conversion to obtain a second logarithmic conversion value;

determining a weight $w_i$ from the first and second logarithmic conversion values by Formula 3;

squaring a difference between the two logarithmic conversion values obtained by the first and second logarithmic conversion means values by Formula 3, and multiplying by the weight $w_i$ to obtain a sum total s; and determining a minimum of a plurality of sum totals s obtained by changing the structural parameter, and determining the structural parameter of the minimum sum total s to be an analytical result.

Also disclosed is a structural parameter analyzing method for determining a structure of a sample by using a measured value of the sample and an expected structural parameter, including:

determining a calculated value corresponding to the measured value according to the expected structural parameter, and making logarithmic conversion of the calculated value to obtain a vector $F_c$ having a first logarithmic conversion value as a matrix element;

making count missing correction to the measured value, subtracting the background strength from the corrected measured value, adding a positive number of less than 1, and making logarithmic conversion to obtain a second logarithmic conversion value vector F having the logarithmic conversion value as a matrix element;

determining a weight matrix W from the first and second logarithmic conversion value vectors $F_c$ and F by Formula 4;

by Formula 4, multiplying a transposition matrix $(F-F_c)^t$, by the weight matrix W. and a difference $(F-F_c)$ between the first and second logarithmic conversion value vectors to obtain a sum total s;

determining a minimum of a plurality of sum totals s obtained by changing the structural parameter, and determining the structural parameter of the minimum sum total s to be an analytical result.

In a structural parameter analyzing method according to another aspect of the invention, as a method for determining the weight $w_i$, data is measured r times under the same condition, Poisson distribution $(y_i+½)$ is not assumed, a variance $\sigma_{ir-1}^2$ at each measuring point (point i) is actually measured, and Formula 5 is used instead of Formula 3.

In a structural parameter analyzing method according to another aspect of the invention, as a method for determining the weight matrix W, data is measured r times under the same condition, Poisson distribution $(y_i+½)$ is not assumed, a variance $\sigma_{ir-1}^2$ at each measuring point (point i) is actually measured, and Formula 6 is used instead of Formula 4.

In a structural parameter analyzing method according to another aspect of the invention, the number m of independent variables in Formula 3 to Formula 6 is set to zero, or omitted from the formulae.

BRIEF DESCRIPTION OF THE DRAWINGS

The present invention will become more fully understood accompanying drawings which are given by way of illustration only, and thus are not limitative of the present invention, and wherein.

DESCRIPTION OF THE PREFERRED EMBODIMENTS

Figure 1:
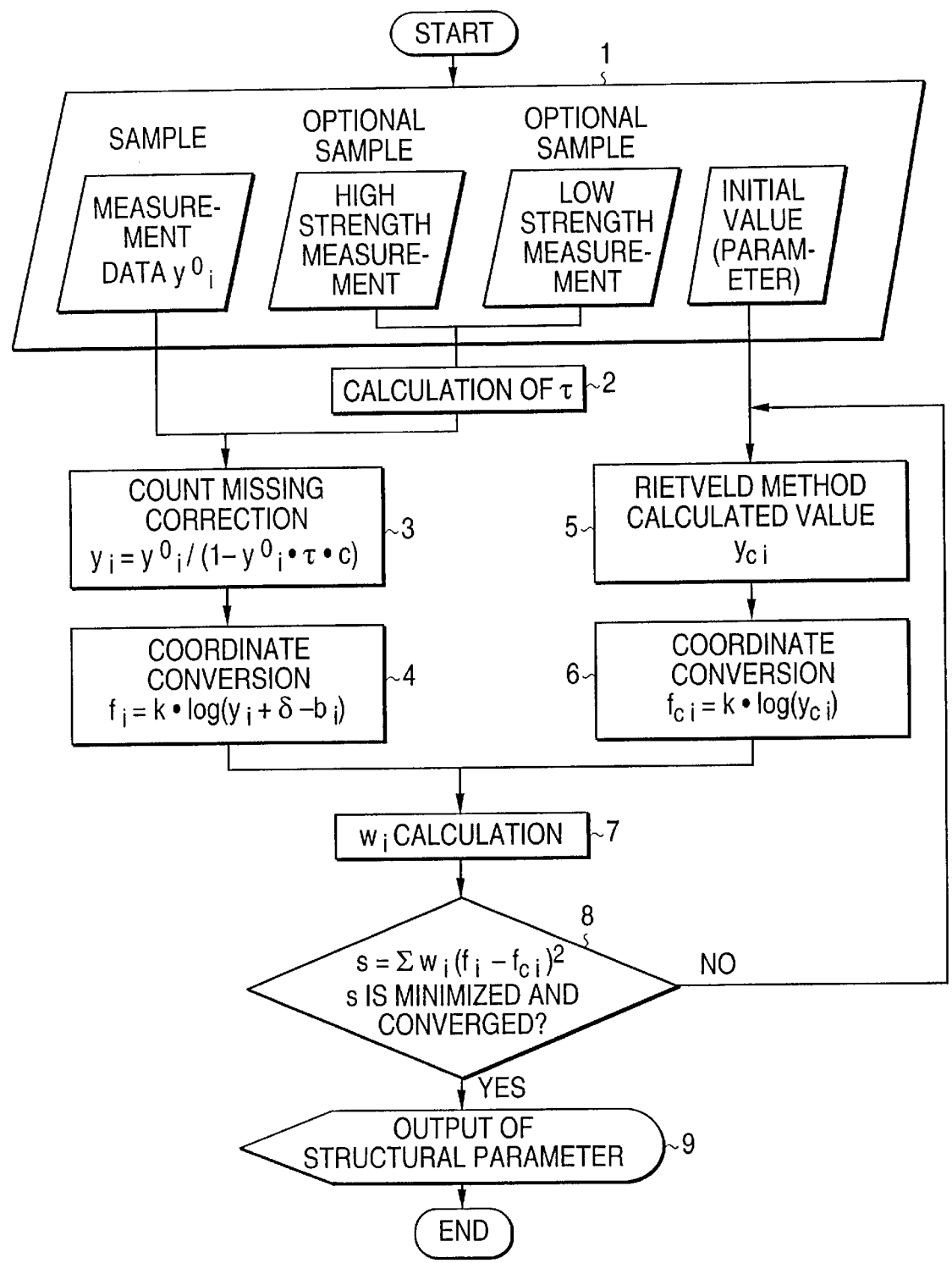
FIG. 1 is a diagram showing flow of an embodiment of the crystal structure parameter analyzing method according to the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Preferred embodiments of the present invention will now be described with reference to the drawings.

Since Formula 3 and Formula 5 are special cases of Formula 4 and Formula 6 where the device function matrix H has no spread (H=E: E is a unit matrix), a non-diagonal term is 0, and a diagonal term is 1, Formula 4 and Formula 16 including the diagonal term will be mainly described. If the device function matrix is a unit matrix, Formula 4 and Formula 6 provide the same result of Formula 3 and Formula 5, respectively.

Thus, one of the embodiments is a crystal structure parameter analyzing apparatus which includes a crystal structure parameter setting unit for previously storing a crystal structure parameter, a data input unit for inputting a measured value of a sample, is calculated value calculation means for obtaining a calculated value corresponding to the measured value according to the crystal structure parameter from the crystal structure parameter setting unit, a first logarithmic conversion means for making logarithmic converting the calculated value, a second logarithmic conversion means for logarithmic converting: a value obtained by subtracting a background strength from the measured value and adding a positive number of less than 1, a sum total calculation means for multiplying the transposition matrix $(F-F_c)^t$ of a difference between two logarithmic conversion value vectors obtained by the first and second logarithmic conversion means by the weight matrix W obtained by the weight means and by a difference $(F-F_c)$ between two logarithmic conversion values obtained by the first and second logarithmic conversion means to obtain a sum total s, a determination unit for determining a minimum of a plurality of sum totals s obtained by the sum total calculation means by changing the crystal structure parameter, and an output unit for outputting the crystal structure parameter of the minimum sum total s.

Further, another embodiment of the crystal structure parameter analyzing apparatus further includes weight calculation means for determining a weight matrix W by Formula 8 from a vector having two logarithmic conversion values obtained by the first and second logarithmic conversion means as a matrix element, wherein the sum total calculation means, by Formula 7, multiplies the transposition matrix $(F-F_c)^t$ of a difference between two logarithmic conversion value vectors obtained by the first and second logarithmic conversion means by the weight matrix W obtained by the weight means and by a difference $(F-F_c)$ between two logarithmic conversion values obtained by the first and second logarithmic conversion means to obtain a sum total s, or comprises correction means for correcting a count missing of the detector for obtaining the measured value, wherein the second logarithmic conversion means subtracts the background strength from the measured value after correcting for count missing and adding a positive number of less than 1 and makes logarithmic conversion.

$$s = (F - F_c)^t W(F - F_c) \quad (7)$$

$$\sum_{SYS} = \left\{ (F - F_c)^t (F - F_c) - (n-m)/n \cdot \sum_{j=1}^{n} \{k^2(y_j + \delta - b_j)^{-2}(y_j + \delta)\} \right\} / n \cdot H^t H \quad (8)$$

wherein s is a residual square sum, i and j are numbers of measuring points, $y_i$ is an i'th measured value after count missing correction, $y_{ci}$ is an i'th calculated value, k is an optional constant, n is a total number of measuring points, m is a number of independent variables $\delta$ is a positive number of less than 1.

$b_i$ is an i'th background strength, W is a weight matrix of n lines and n rows, F is a vector of n lines and 1 row having $k \cdot \log(y_i+\delta-b_i)$ as a matrix element, $F_c$ is a vector of n lines and 1 row having $f_{ci}=k \cdot \log(y_{ci})$ as a matrix element, $\Sigma POI$ is a covariation matrix of n lines and n rows having $k^2(y_i+\delta-b_i)^{-2}(y_i+\delta)$ as a diagonal element due to white noise (Poisson distribution), $\Sigma SYS$ is a covariation matrix of n lines and n rows due to systematic error, H is a device function matrix (spread function matrix due to measuring device) of n lines and n rows, $H^t$ is a transposition matrix of H.

Further, one of the embodiments of the invention is a crystal structure parameter analyzing method, in which a calculated value corresponding to the measured value is determined according to the expected structural parameter, and the calculated value is logarithmic converted to obtain a vector having a first logarithmic conversion value as a matrix element, the background strength is subtracted from the measured value and a positive number o less than 1 is added and then logarithmic converted to obtain a vector having a second logarithmic conversion value as a matrix element, the structural parameter is changed until the first and second logarithmic conversion values are sufficiently close to each other, and the structural parameter at the close logarithmic conversion values is determined to be an analytical result, or, a calculated value corresponding to a measured value is determined according to an expected crystal structure parameter, the calculated value is logarithmic converted to obtain a vector having a first logarithmic conversion value as a matrix element, the measured value is corrected for count missing of the detector, the background strength is subtracted from the corrected measured value and a positive number of less than 1 is added, and the result is logarithmic converted to obtain a vector having a second logarithmic conversion value as a matrix element, a weight matrix W is obtained by Formula 8 from vectors having the first and second logarithmic conversion values as matrix elements, the transposition matrix $(F-F_c)^t$ of a difference between vectors having two logarithmic conversion values obtained by the first and second logarithmic conversion means as matrix elements, the weight matrix W obtained by the weight means, and a difference $(F-F_c)$ between the vectors having two logarithmic conversion values obtained by the first and second logarithmic conversion means as matrix elements are multiplied to obtain a sum total s, a minimum of a plurality of sum totals s obtained by changing the crystal structure parameter is determined, and the crystal structure parameter of the minimum sum total is outputted.

The principle of the present invention will be described.

First, experimentally, magnitudes of errors have been repeatedly measured, and found that errors can be represented almost exactly when it is assumed that there exist the following two kinds of errors, statistical variation and systematic error.

1. Statistical variation: an accidental error due to intensity variation theoretically occurring in light sources such as X-ray, and in the prior art methods, errors have been all assumed to be statistical variation.

2. Systematic error: occurs in the measuring system due to errors such as the sample is not ideal, the shape is not good, or the sample is difficult to be pulverized; diffraction; and/or error of the analytical apparatus itself, which in most cases, is several to 10 times greater than statistical variation. Then, where a measured value at a measuring is point i is $y_i$, and a background strength is $b_i$, when $b_i$ is subtracted from $y_i$, and a positive number $\delta$ of less than 1 is added $(y_i+\delta-b_i)$ and logarithmic converted as $\log(y_i+\delta-b_i)$, it is found that almost constant systematic error is present in the logarithmic conversion value in all measuring points. It is considered that the statistical variation is represented by a Poisson distribution, and the magnitude of variance is $y_i+\delta$ ($\delta$ is a positive number of less than 1).

When there are a number (r times) of measured data under the same conditions, such as when the measured data is integrated, a Poisson distribution is not assumed and $\sigma_{ir-1}^2$ of each measuring point (point i) is actually measured. The value $(y_i+\frac{1}{2})$ of Formula 3 and Formula 4 is replaced with actually measured $r\sigma_{ir-1}^2$ and Formula 5 and Formula 6 are used, thereby including information of output variation of X-ray source and dark current of the detector which improves accuracy.

Further, in the systematic error, there exists a spread of diffraction line due to the measuring device. In the powder diffraction method, Si or $LaB_6$ is often mixed and coated as an angle standard sample. Since these are sufficiently good in crystallinity and show a spread (device function matrix Ho) of the device and light source, this information is utilized. In the analysis, first, only Si or $LaB_6$ mixed and coated as an internal standard is analyzed to determine a profile, which depends on $2\theta$. This profile is used as a matrix element in the row direction to obtain a device function matrix Ho. Where a half width in the row direction of the actually measured device function matrix Ho is $ho_i$ and a half with in the row direction of the device function matrix H used in the calculation is $h_i$, the closer $h_i$ is spread to the actually measured $h_{oi}$, the more the resolution is improved. But since this corresponds to narrowing of slits of the diffraction apparatus, S/N ratio is decreased. Therefore, it is effective to continuously change $h_i$ according to S/N ratio $f_{min}/\sigma_{POI}$. Device function H used in the actual calculation is calculated according to Formula 9. The center of mass is adjusted to move on the diagonal of the matrix so that the measuring angle ($2\theta$ center of mass of diffraction line) is not moved by multiplying with the device function H, and the sum of each row is normalized to 1.

$$h_i = h_{oi} <1-p\{\sigma_{POIi}/(f_i-f_{min})\}> \quad (9)$$

$$\sigma_{POIi} = <k^2(y_i+\delta-b_i)^{-2}(y_i+\delta)>^{1/2}$$

or when there are a plurality (r times) of measured data under the same condition, $$\sigma_{POIi} = <k^2(y_i+\delta-b_i)^{-2}(r\sigma_{ir-1}^2)>^{1/2}$$

wherein $f_{min}$ is minimum value of measured value (after coordinate conversion), p is a constant to maintain S/N ratio at a constant value, r is a number of measurements under the same condition.

From these matters, due to the law of propagation of errors, where the residual square sum is s, the weight matrix is W, and the number of total measuring points is n, it is considered to be the best in the crystal structure analysis that using Formula 7 ($s=(F-F_c)^t W(F-F_c)$) and Formula 8 ($W=(\Sigma_{POI}+\Sigma_{SYS})^{-1}$, $\Sigma_{SYS}=[(F-F_c)^t, (F-F_c)-(n-m)/\Sigma_j(k^2(y_j+\delta-b_j)^{-2}(y_j+\delta))]/n.H^tH$), the convergence calculation is used to minimize the residual square sum of the logarithmic conversion value vectors F and $F_c$ to determine the calculated value vector $F_c$.

Figure 7:
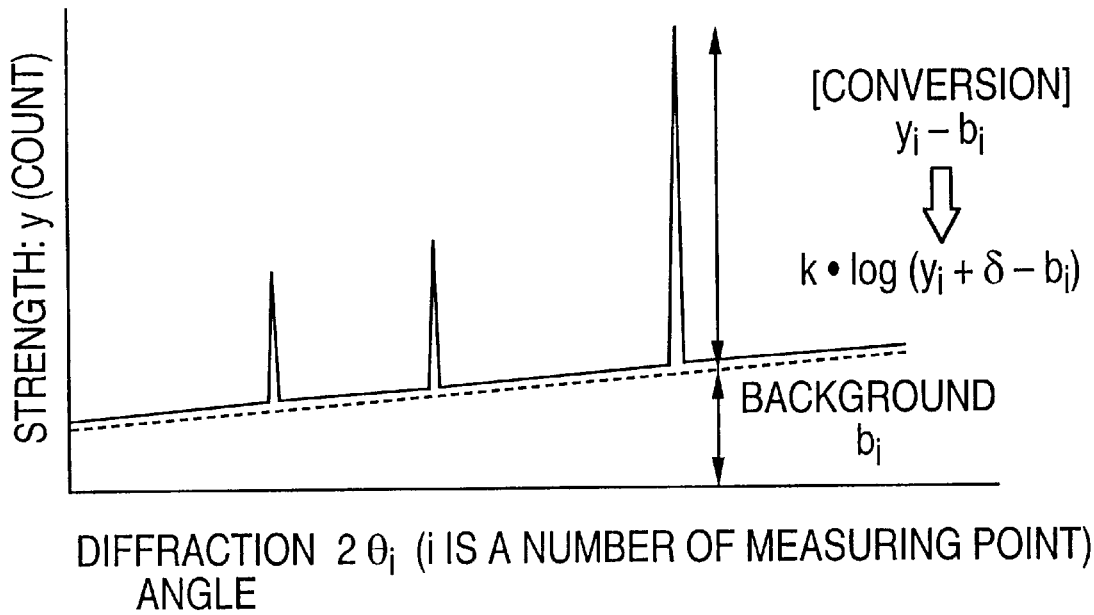
FIG. 7 is a diagram showing an example of a measured data and background strength vector in diffraction spectrum processing.

With Formula 8, as is, the weight matrix W of each measuring point may come out from the spectrum norm=1 represented by Formula 10, to cause it to be strictly 1, a coefficient is multiplied for re-normalization. In Formula 3 and Formula 5 having no nondiagonal term of weight matrix, it is normalized to $\Sigma_{Wi}=1$. Determination of the background strength $b_i$ is basically optional, however, it is normally drawn as a straight line as shown in FIG. 7 to avoid deformation of the diffraction line profile, and it is set as high as possible within the range satisfying Formula 11 ($k \cdot \log(y_i+\delta-b_i) \geq (k^2(y_i+\delta-b_i)^{-2}(y_i+\delta))$) at all measuring points.

$$\text{Spectrum Norm } \|W\|i=1 \quad (10)$$

$$k \cdot \log(y_i+\delta-b_i) \geq (k^2(y_i+\delta-b_i)^{-2}(y_i+\delta)) \quad (11)$$

Further, a certain effect can be obtained even without multiplying the weight matrix at each measuring point (even with W=E: E is a unit matrix).

Still further, in Formula 3 to Formula 6, Formula 8 and the like, the number m of independent variables is subtracted from the number n of total measuring points, which is for strictness. However, in effect, since the number m of independent variables (parameters) such as lattice constant, half width, atomic coordinate, freedom of background setting are small in number and negligible as compared with the number n of total measuring points which is very large, a sufficient effect can be obtained even with m=0 or omitted from the Formula.

In the past, since errors have been all assumed to be statistical errors, high-strength peak errors including much systematic errors are excessively emphasized by the least square method, and low-strength peaks are relatively neglected to coincide measured values of high strength with calculated values. However, in the present invention, by introducing the systematic errors and making logarithmic conversion, it is possible to exactly evaluate information of low-strength peaks including much information of light elements and trace ingredients without excessively emphasizing high-strength peak errors.

Further, as to the resolution, by introducing the nondiagonal term of weighting matrix, although in effect being limited by the crystallinity of the standard sample, in principle, the resolution is continuously improved as far as the measuring time is allowed.

EMBODIMENTS

Embodiments of the present invention will be described with reference to the drawings. In these embodiments, logarithmic conversion (logarithmic coordinate conversion) is applied to the measured value $y_i$ and calculated value $y_{ci}$ as shown in FIG. 7 in the Rietveld crystal structure analysis by a generally-used powder X-ray diffraction apparatus.

Embodiment 1

Figure 5:
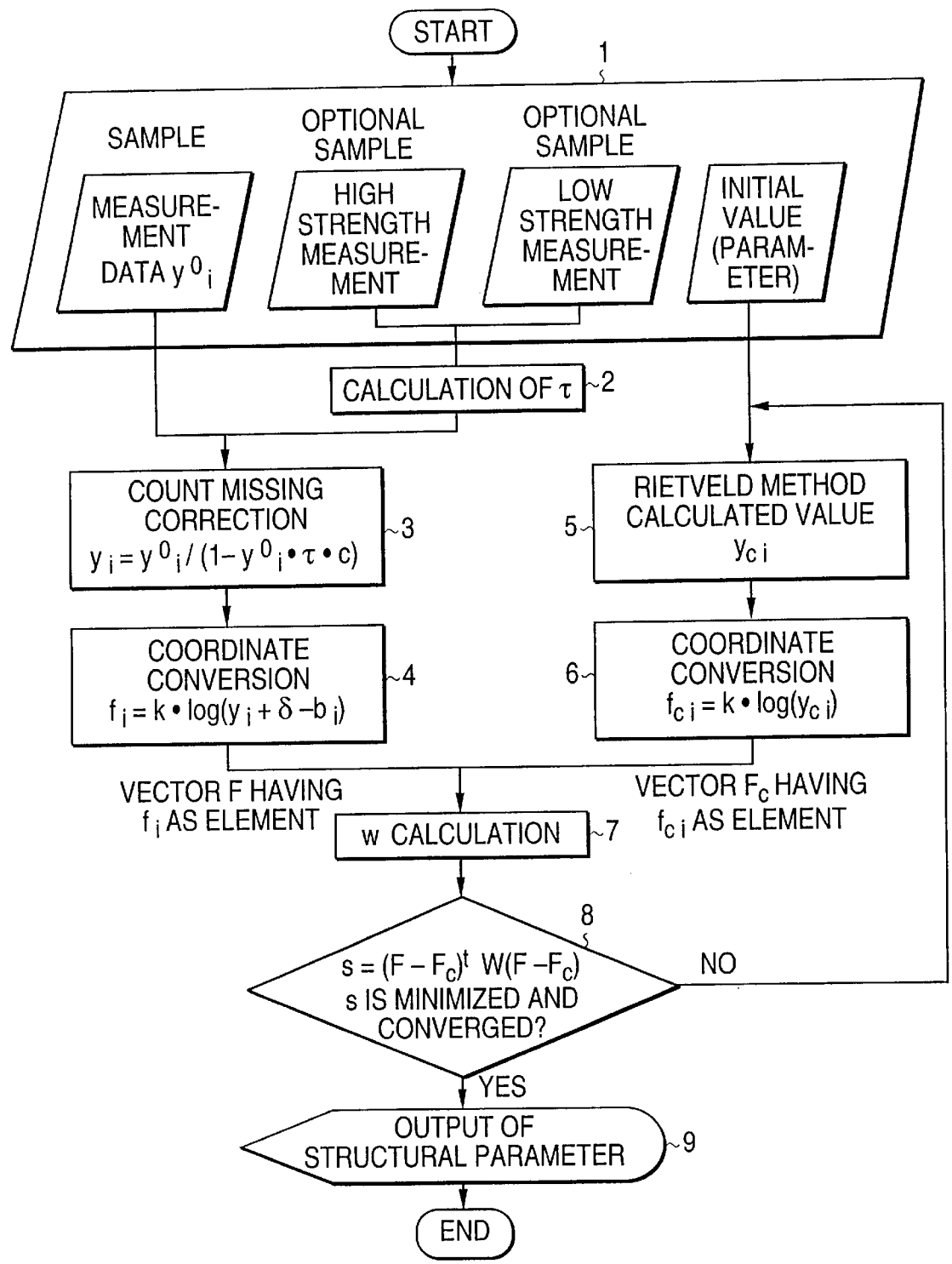
FIG. 5 is a diagram showing flow of an embodiment of the crystal structure parameter analyzing method according to the present invention.

First, an embodiment of the crystal structure parameter analyzing method will be described with reference to FIG. 5. As shown in FIG. 5, in step 1, a measured data $y^o_i$ of a sample obtained from a detector by an X-ray diffraction method or a neutron diffraction method, and a crystal structure parameter expected for the sample are prepared. Further, since the detector has a dead time of count missing of the number of photons if a large number of photons are incident, as necessary, to correct for count missing of diffraction line strength by a dead time of the detector, a measured data of different strengths when irradiated X-ray strength or irradiated neutron strength of an optional material is changed is prepared. In step 2, a dead time τ of the detector is calculated. The measured data $y^o_i$ is inputted, for example, to a computer, as necessary using the dead time obtained in step 2, count missing correction of i'th measured data $y^o_i$ is made in step 3, and the corrected value is determined as an i'th measured value $y_i$. Here, a symbol c in FIG. 5 is a form factor by the detector circuit, and for the correction calculation, for example, the following $y_i = y^o_i/(1-y^o_{i.\tau.c})$ of Formula 20.

$$y_i = y^o_i/(1-y^o_{i.\tau.c}) \quad (12)$$

Next, in step 4, by Formula 13 ($f_i = k \cdot \log(y_i+\delta-b_i)$), using an i'th background strength $b_i$, the i'th measured value $y_i$ is converted into a vector F having an i'th logarithmic conversion value as a matrix element. However, while δ is a positive number of less than 1, since it is generally unknown, it may be processed as δ=½ for simplicity. Except for the case where the measuring time is extremely short, δ can be omitted or of δ=0 can be used.

$$f_i = k \cdot \log(y_i+\delta-b_i) \quad (13)$$

In this conversion, so that the program of Rietveld method according to the value vector F after coordinate conversion can be used, as is, on the same order of the measure value $y_i$ or $y^o_I$ (for example, normally 5000–6000 counts), an optional constant k (for example, about 600) is used. Further, as the background strength $b_i$, within the range satisfying Formula 11 as shown in FIG. 7, it is set as high as possible to a straight line. Natural logarithm is used with the base of e, and any base of logarithm can be absorbed by setting of the constant k.

After that, using initial crystal structure parameters such as lattice constant and space group prepared in step 1 by the prior art Rietveld method, in step 5, an i'th is calculated value $y_{ci}$ corresponding to the i'th measured value $y_i$ is calculated by the strength formula by the Rietveld method as in the prior art.

In step 6, the i'th calculated value $y_{ci}$ is converted by Formula 14 ($f_{ci} = k \cdot \log(y_{ci})$) into a vector $F_c$ having the i'th logarithmic conversion value as a matrix element. Also in this conversion, for the same reason as in step 4, the same constant k is used and natural logarithm is used.

$$f_{ci} = k \cdot \log(y_{ci}) \quad (14)$$

Then in step 7, using the logarithmic conversion value vector F obtained in step 4 and the logarithmic conversion vector $F_c$ obtained in step 6, a weight matrix W at each measuring point i is calculated by Formula 8. As to the weight matrix W, although the value calculated by Formula 8 may come out from the spectrum norm=1, it is re-normalized to 1 by multiplying a coefficient.

After that, in step 8, to the i'th logarithmic conversion value vector F obtained in step 4 and the i'th logarithmic conversion value vector $F_c$, using the i'th weight matrix W obtained in step 7, a determination is made as to whether or not the residual square sum s in Formula 15 ($s=(F-F_c)^tW(F-F_c)$), equivalent to Formula 7, is minimized or converged, for example, in a computer. When it is converged within a predetermined range, step 9 is executed, or when it is not converged, an instruction is made to repeatedly execute the steps (5–8) after step 5. That is, in step 5, the crystal structure parameter is changed according to the residual square sum s to re-determine the calculated value vector $F_c$. By repeating steps 5–8 as above, it is assumed that it will not be further minimized if a crystal structure parameter such as atomic configuration is changed.

$$s=(F-F_c)^tW(F-F_c) \quad (15)$$

While solution of the nonlinear least square sum method to determine the structural parameter in Formula 15 is optional, since there may be a case where the matrix is not positive definite if a non-diagonal term is introduced into the weight matrix W, or high resolution spectrum cannot be displayed if there is a non-diagonal term, it can be solved by decomposition as follows. In the solution to form the observation equation, where the vector having the structure parameter to be determined as a matrix element is X, a differential (Jacobian) matrix in the prior art Rietveld method is $A^0$, a differential matrix in the present invention for converting the observed value into logarithm is A, and the observed value vector after logarithmic conversion given as F by Formula 24 is almost equal to AX. In the differential matrix, A can be approximated by Formula 7, the solution X to be determined is given by Formula 18. Σ in the form of band matrix is decomposed by combining revised Cholesky decomposition $UDU^t$ with the diagonal matrix G. Wherein U is an upper triangular matrix, D is a diagonal matrix, and G is a matrix to normalize the sum of each line of the upper triangular matrix to 1. Since the weight matrix W' becomes a diagonal form when decomposed as in Formula 18, Formula 19 is solved, and substitution is made. High-resolution observed value F' and calculated value $(GU)^1F_c$ become spectrum displayable as in Formula 20.

$$=AX \quad (16)$$

$$A=LA^0 \quad (17)$$

wherein L is a diagonal matrix of n lines and n rows having $k \cdot \log(y_i)/y_i$ as a diagonal element.

$$A^tWAX=A^tWF \quad (18)$$

$$A^t\Sigma^{-1}AX=A^t\Sigma^{-1}F$$

$$A^t(U^tDU)^{-1}AX=A^t(U^tDU)^{-1}F$$

$$((GU)^{-1}A)^tGD^{-1}G((GU)^{-1}A)X=((GU)^{-1}A)^tGD^{-1}G((GU)^{-1}F)$$

$$(GU)^{-1}A=A' \quad (19)$$

$$(GU)^{-1}F=F'$$

$$GD^{-1}G=W'$$

$$A'^tW'A'X=A'^tW'F' \quad (20)$$

In step 9, the crystal structure parameter corresponding to the calculated value vector $F_c$ (i=1 to n) when the residual square sum s is minimized and converged is determined to be a final crystal structure parameter, and the finally obtained crystal structure parameter is outputted from the computer. This output is used, for example, for a screen display device or a printer.

Embodiment 2

Next, a crystal structure parameter analyzing apparatus for calculating a crystal structure from a diffraction spectrum using the above-described crystal structure parameter analyzing method will be described with reference to FIG. 6.

Figure 6:
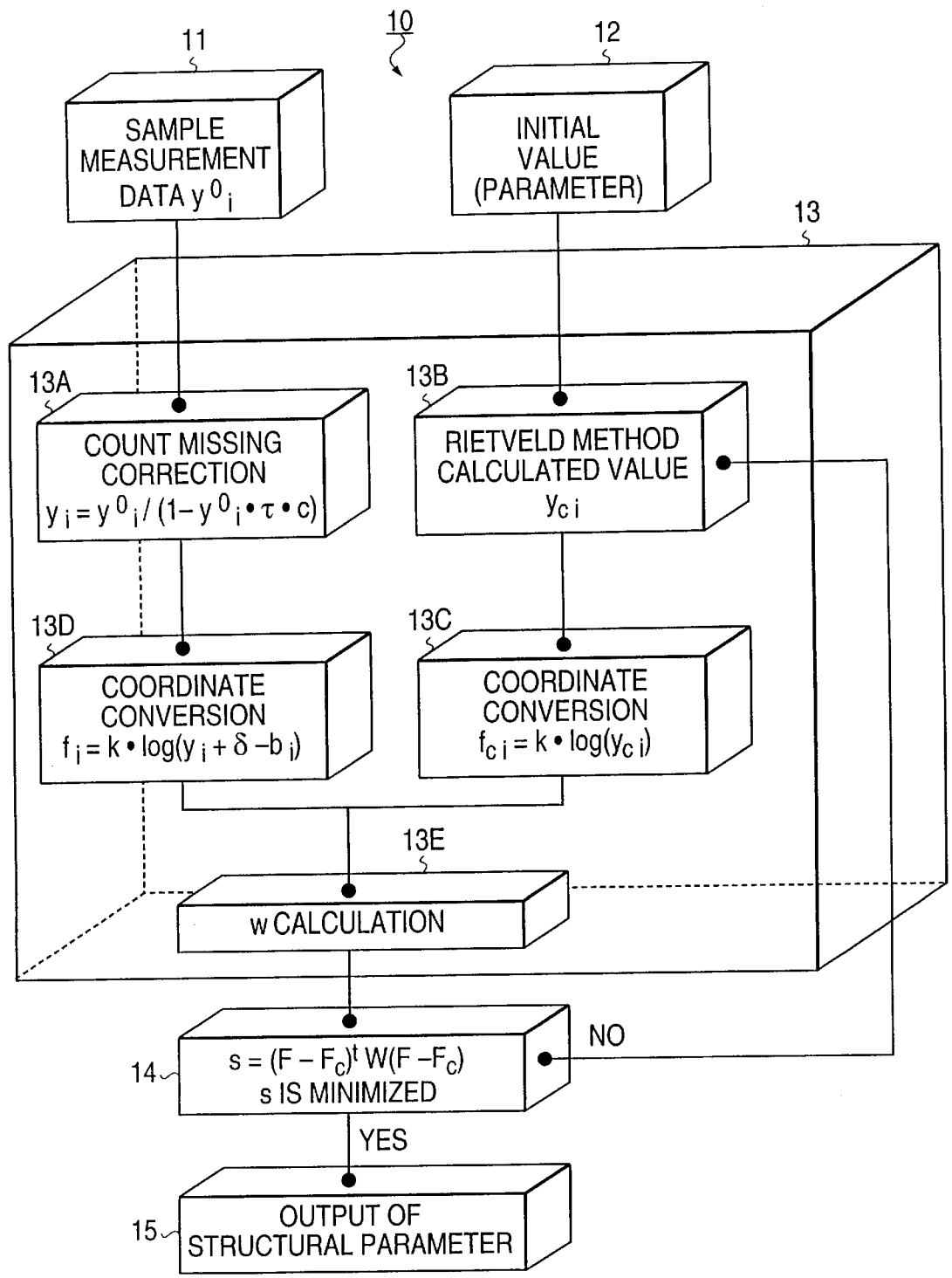
FIG. 6 is a diagram showing the structure of an embodiment of the crystal structure parameter analyzing apparatus according to the present invention.

In FIG. 6, a crystal structure parameter analyzing apparatus 10 comprises a data input unit 11, a crystal structure parameter setting unit 12, a calculation unit 13, a determination unit 14, and an output unit 15. The calculation unit 13 comprises a correction unit 13A, a calculated value calculation unit 13B, a first logarithmic conversion unit 13C, a second logarithmic conversion 13D, and a weight matrix calculation unit 13E. A residual square sum s is obtained using above-described Formula 4, Formula 6, Formula 7 or Formula 8.

Both the data input unit 11 and the crystal structure parameter setting unit 12 are connected to the calculation unit 13, the data input unit 11 is to input a measured data $y^0_i$ of the sample obtained by a detector (not shown) to the calculation unit 13, the crystal structure parameter is to previously store an expected crystal structure parameter (initial value) by the prior art Rietveld method and input it to the calculation unit 13. The crystal structure parameter comprises the lattice constant, the space group, the half width of peak (an appropriate setting of this half width parameter gives faster convergence calculation), and the like, as described above.

The calculation unit 13 is set with Formula 12 as a calculation formula for count missing correction of the detector; Formula 13 and Formula 14 as calculation formulae of coordinate conversion (logarithmic conversion), a formula for Rietveld calculation (omitted); Formula 8 as a weighting matrix calculation formula; and Formula 15 (equivalent to Formula 7) as a calculation formula for the residual square sum.

Specifically, the correction unit 13A, to correct for count missing of diffraction line strength due to a dead time of the detector, calculates a dead time τ of the detector using strong and weak measured data when the irradiation X-ray strength or irradiation neutron strength of an optional material, count missing correction of measured data $y^0_i$ of the sample is made by Formula 12 using the obtained dead time τ, and the corrected value is given as the measured value $y_i$ to the logarithmic conversion unit 13D. The calculated value calculation unit 13B, using initial crystal structure parameters such as lattice constant and space group, calculates a calculated value $y_{ci}$ corresponding to the measured value $y_i$ using the strength formula by the Rietveld method same as the prior art, and the result is given to the logarithmic conversion unit 13C. The logarithmic conversion unit 13C converts the calculated value $y_{ci}$ to a logarithmic coordinate value vector $F_c$ by Formula 14. On the other hand, the logarithmic conversion unit 13D converts the measured value $y_i$ into a logarithmic coordinate value vector F by Formula 13 using the background strength $b_i$ and a positive number δ of less than 1. The weight matrix calculation unit 13E, using the logarithmic conversion value vector F and the logarithmic conversion value vector $F_c$, calculates a weight matrix W at each measuring point i by Formula 8. The weight matrix W is further normalized to spectrum norm=1. The calculation unit 13 determines a residual square sum (sum total) s by Formula 15 using the thus obtained weight matrix W and the two logarithmic conversion vectors F and $F_c$.

The determination unit 14 determines whether or not the measured value F and the calculated value $F_c$ after logarithmic conversion are sufficiently close to each other by whether or not the residual square sum s is minimized and converged. If not sufficiently close the determination unit 14, instructs the calculation unit 13 to make recalculations by changing the crystal structure parameter. If sufficiently close, the determination unit 14 instructs to input the crystal structure parameter to the output unit 15. Thus, the determination unit 14 determines a minimum of a plurality of residual square sums obtained by the calculation unit 13.

The output unit 15 is to inform the crystal structure parameter of the output result to the operator or the like, for example, a screen display device or a printer.

The crystal structure parameter analyzing apparatus 10 of the above construction is not limited to the above arrangement, but can be one which makes logarithmic coordinate conversion of the measured data $y_i$ and the calculated value $y_{ci}$ obtained by the Rietveld method from a crystal structure parameter as the initial value to obtain a crystal structure parameter which reproduces the actually measured logarithmic conversion value vector F most exactly. For example, it is possible to construct the data input unit 11 and the crystal structure parameter setting unit 12 in a single input device. Further, it is also possible to incorporate the determination unit 14 in the calculation unit 13.

Next, operation of the above crystal structure parameter analyzing apparatus 10 will be described with reference to analysis examples of, for example, α—$Al_2O_3$ (NBS strength standard sample NIST1976), $Y_2O_3$-stabilized zirconia (containing 7.36 mole % $Y_2O_3$, sintered at 1400° C., 1 h, and kept at 1000° C. for 5500 h) and $C_{ao}.9La o.1TiOx$.

First, in the data input unit 11, a step scan measured data $y°_i$ by a powder X-ray diffraction method is integrated, measured, and set. The measurement uses a powder diffraction wide-angle goniometer, and as an X-ray source, a water-cooled rotary counter cathode type with an input power of 18 KVA is used, and a monochromator is used in the X-ray detection unit. Measurement conditions are: Cu target, diffraction angle 2θ range 20–145°, 2θ feed width 0.03° per 1 step, measuring time of 1 second per 1 step, the measurement is repeated 10 times and integrated. Optical conditions are: divergence slit and scatter slit are 1°, and light receiving slit is about 0.15 mm.

Further, previously expected lattice constant, space group, and the like are set by the crystal structure parameter setting unit 12. Initial values of α-alumina are assumed as: a=4.763 Å, c=13.003 Å, space group R*3C, 12 Al atoms occupying (0,0,0; ⅓,⅔,⅔; ⅔,⅓,⅓)+(0,0,z; 0,0,z*; 0,0,½+z; 0,0,½−z); z=0.35, 18 O atoms occupying (0,0,0; ⅓,⅔,⅔; ⅔,⅓,⅓)+(0, x,¼; x*,x*,¼; x*,0,¾; 0,x*,¾; x,x,¾); x=0.31, wherein the symbol * represents the reverse (minus) direction without of it, which is normally used instead of an upperline.

The initial values of lattice constant of YSZ (yttriastabilized zirconia) are in a cubic phase (C phase) and assumed as a=5.128 Å, space group Fm*m, 4×(1−0.0736) Zr atoms occupying (0,0,0; 0,½,½; ½,0,½, ½,½,0;)+(0,0,0; 0,½, ½; ½,0,½; ½,½,0), 4×0.0736 Y atoms occupying (0,0,0; 0,½,½; ½,0,½; ½,½,0)+(0,0,0; 0,½,½; ½,0,½; ½,½,0), 8×(1−0.0736/4) O atoms occupying (¼,¼,¼; ¼,¼,¾)+(0,0,0; 0,½, ½; ½,0,½; ½,½,0). The symbol * means the same as above.

In a metastable tetragonal crystal (t' phase), the values are a=3.5866 Å, c=5.1791 Å, space group $P4_2$/nmc, 2×0.0736 Zr atoms occupying (0,0,0; ½,½,½), 2×(1−0.0736) Y atoms occupying (0,0,0; ½,½,½), 4×(1−0.0736/4) O atoms occupying (0,½,z; 0,½,z+½; ½,0,z*+½; ½,0,z*); z=0.215. The symbol * means the same as above.

In a metastable tetragonal crystal (t" phase), the values are a=3.647 Å, c=5.1589 Å, space group $P4_2$/nmc, 2×0.0736 Zr atoms occupying (0,0,0; ½,½,½), 2×(10.0736) Y atoms occupying (0,0,0; ½,½,½), 4×(1−0.0736/4) O atoms occupying (0,½,z; 0,½,z+½; ½,0,z*+½; ½,0,z*); z=0.23. The symbol * means the same as above.

The above-set sample measured data $y°_i$ and the crystal structure parameter are inputted into the calculation unit 13.

The calculation unit 13, after making count missing correction, obtains the vector $F_c$ having a value of vector F obtained by logarithmic conversion by Formula 17 and the value obtained by logarithmic conversion of the calculated value $y_{ci}$ by the Rietveld method using Formula 22 as a matrix element.

In the determination unit 14, a determination is made as to whether or not the measured value vector F and the calculated value $F_c$ are sufficiently close to each other. The calculation procedure from the calculation of the calculated value $F_c$ by the Rietveld method in the calculation unit 13 is repeated until sufficiently close values are obtained. When the measured value vector F and the calculated value $F_c$ are sufficiently close, the calculation result of analysis is outputted from the output unit 15. When the output unit 15 comprises a printer, the calculation result is printed and outputted.

An analytical result of α−$Al_2O_3$ will be described below.

The in-lattice coordinate x of oxygen has been determined as 0.30623±0.00009. The value by the prior art Rietveld method, according to a literature (Hill, R. J. and Madsen I. C., Diffract., vol. 2, 146(1987), is about 0.3068±0.001. From this fact, with the analyzing method and analyzing apparatus according to the present invention, the position determination accuracy of a −$Al_2O_3$ is improved by several tens of times over the prior art. Further, a literature (Lewis, J., Schwarzenbach, D., and Flack, H. D., Acta Crystallogr., A38, 733(1982) reports a value by the single crystal structure analyzing method by a 4-axis diffractometer which is considered to be close to the true value as 0.30624±0.00004, which is in very good agreement with the above value by the analysis according to the present invention.

Further, as to $Y_2O_3$ stabilized zirconia (YSZ), one containing 7.36 mole % of $Y_2O_3$ and heated at 1000° C. for 5500 hours cannot be analyzed by the prior art method, but can be analyzed as a three-phase mixture by the analyzing method according to the present invention, in which C phase can be analyzed as lattice constant a=5.14132 Å, estimated content of 16%, t' phase is analyzed as a=3.63130 Å, c=5.15695 Å, internal coordinate of oxygen of 0.235, and estimated content of 52%, and t" phase is analyzed as a=3.63165 Å, c=5.13593 Å, internal coordinate of oxygen of 0.209, and estimated content of 31%.

From the above, it is found that the present invention improves the accuracy by a factor of several tens of times for the case of a —$Al_2O_3$, and enables analysis of a difficult-analysis sample for the case of YSZ.

Analytical results of $C_{ao}.9L_{ao.1}TiO_x$ by introducing a device function into the non-diagonal term will be described below.

Figure 8:
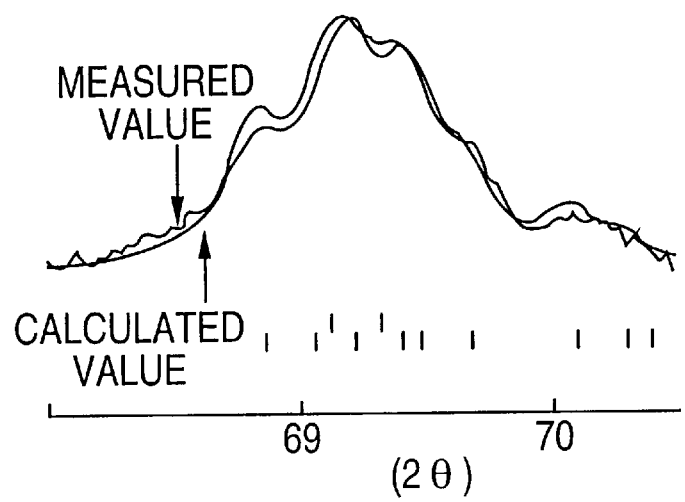
FIG. 8 is a graph enlarged in the axis of abscissas of profile fitting when device function is not considered.
Figure 9:
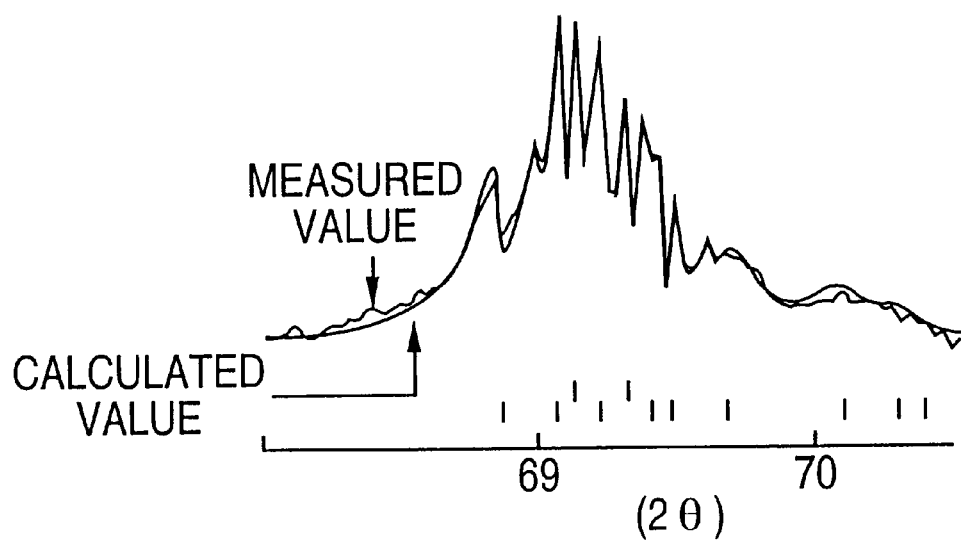
FIG. 9 is a graph enlarged in the axis of abscissas of profile fitting when device function is considered.

The measurement conditions are the same as above. A device function matrix is determined from a profile of diffraction line of an Si(NBS640b standard sample) coated to a small thickness on the-sample surface, using which $C_{ao}.9L_{ao.1}TiOx$ has been analyzed. FIG. 8 is a profile fitting, enlarged in the direction of the axis of abscissas when the device function is not considered, FIG. 9 shows the case of the present invention considering the device function. While in the case of not considering the device function in FIG. 8 the diffraction lines are overlapped with each other. In FIG. 9 of the present invention, the substantial resolution is improved and 8 peaks are clearly separated so that the positions of the diffraction lines can be determined with good accuracy. There is no danger of wrong assignment or convergence to a minimal point rather than a minimum point. In addition, one seen as a single peak in FIG. 7 is separated into 8 lines in FIG. 9 by the improvement of resolution.

On the other hand, a resolution of synchrotron orbital radiation using an accelerator requiring a large-scale facility (literature: Haruo Ozawa et al.: Yoshihiko Uno "Proceedings of report on X-ray powder diffractometer by radiation") is reported as a half width of 0.0580 (d=0.00704 Å-1) when 2θ is in the vicinity of 25.4°. Since, in the analytical example according to the present invention, when 2θ is in the vicinity of 70.0°, the half width is 0.0036° (d=0.00006 Å$^{-1}$), which is 10 to 100 times higher than the resolution of synchrotron radiation.

Other embodiments of the present invention will be described with reference to FIGS. 1 and 2.

Embodiment 3

Figure 2:
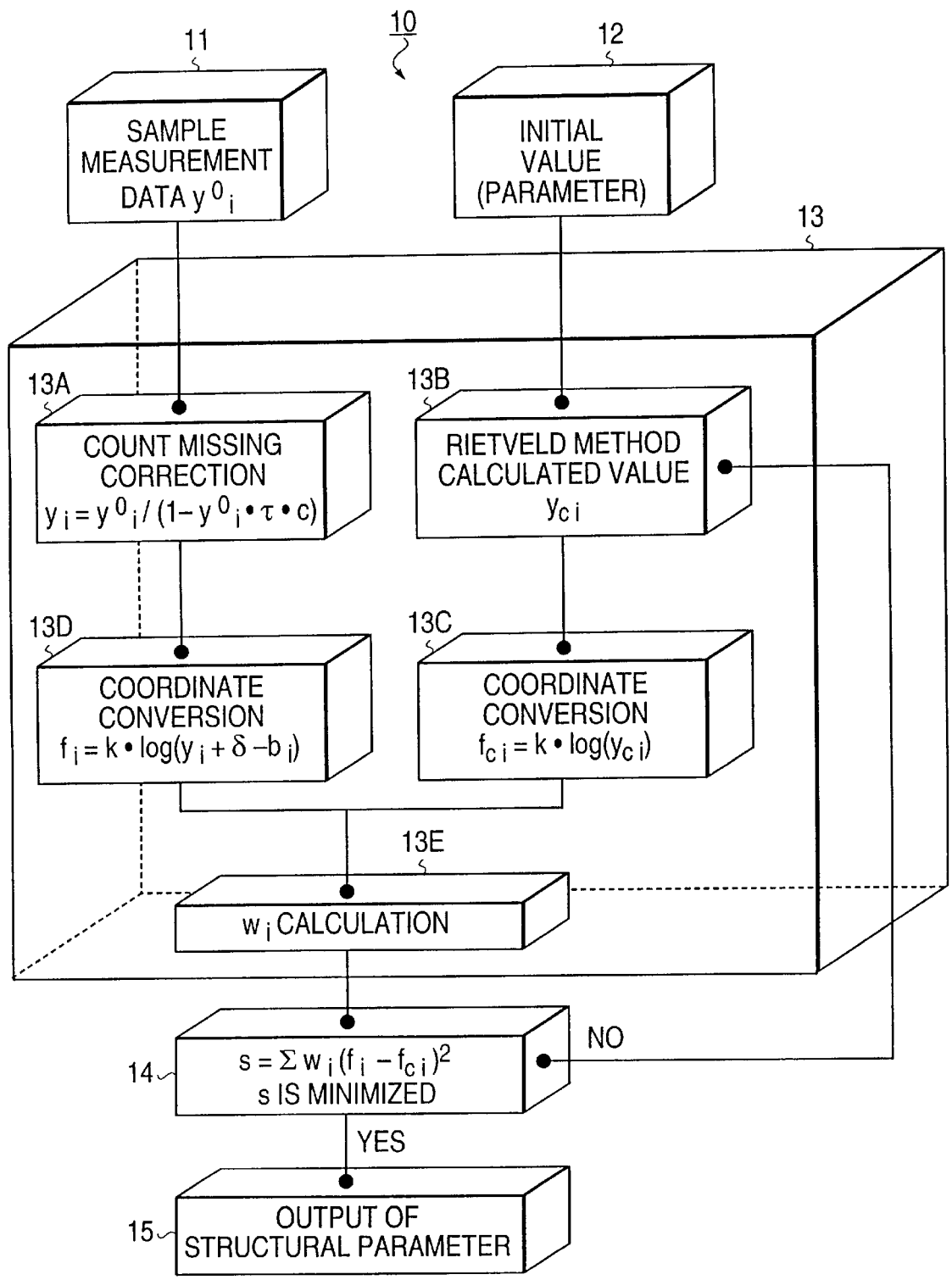
FIG. 2 is a diagram showing the structure of an embodiment of the crystal structure parameter analyzing apparatus according to the present invention.

In the crystal structure parameter analyzing method shown in FIG. 1, the weight matrix calculation processing from the analyzing method shown in FIG. 5 by Formula 8 in step 7 is assumed as only the diagonal term, as H=E (E is a unit matrix), Formula 3 is used instead of Formula 8. Consequently, in step 8, using the calculation of residual square sum s by Formula 21 ($s=\Sigma W_i(f_i-f_{ci})^2$), a determination is made, for example, in a computer as to whether or not the residual square sum s is minimized or converged, to the logarithmic conversion value $f_i$ obtained in step 4 and the logarithmic conversion value $f_{ci}$ obtained in step 8. When converged, step 9 is carried out, when not converged, it is instructed to repeatedly carry out steps (5, 6, 7, 8) after step 5. Other steps are the same as in FIG. 5. As in this example, even without using the weight matrix W by Formula 8, by whether or not the residual square sum s is minimized and converged using Formula 29, a determination is made as to whether or not the measured conversion value $f_i$ and the calculated conversion value $f_{ci}$ are sufficiently close to each other, the procedure from the calculation by the Rietveld method is repeated until the values are sufficiently close to each other. The crystal structure can be analyzed with higher accuracy then the prior art, even though the resolution is not improved as shown in FIG. 8. The weight $W_i$ is practically no problem even if the sum is not 1, however, strictly, it may be normalized as $\Sigma W_i=1$.

$$s = \sum_{i=1}^{n} W_i(f_i - f_{ci})^2 \qquad (21)$$

Embodiment 4

Next, a crystal structure parameter analyzing apparatus for calculating the crystal structure from a diffraction spectrum using the crystal structure parameter analyzing method of the above-described FIG. 1 will be described with reference to FIG. 2 which shows the structure of the apparatus. In the crystal structure parameter analyzing apparatus shown in FIG. 2, the analyzing apparatus shown in FIG. 9 is changed to one which calculates only the diagonal term by the weight matrix calculation unit 13E by Formula 3. Consequently, by determining in the determination unit 14 whether or not the residual square sum s is minimized and converged, a determination is made as to whether or not the measured value $f_i$ and the calculated value $f_{ci}$ after logarithmic conversion obtained by the individual logarithmic conversion units 13D and 13C are sufficiently close to each other. When not sufficiently close, an instruction is made to calculation unit 13 to recalculate by changing the crystal structure parameter. When close to each other, an instruction is made to input the crystal structure parameter into the output unit 15. Other structure is the same as in FIG. 6. Even without using the weight matrix W by Formula 8 as in the present embodiment, the crystal structure can be analyzed with improved accuracy over the prior art by determining whether or not the measured value $f_i$ and the calculated value $f_{ci}$ are sufficiently close to each other using weight of Formula 21 whether or not the residual square sums is minimized and converged, and calculation procedure from the Rietveld method is repeated until the values are sufficiently close to each other.

Next, still further embodiments of the present invention will be described with reference to FIGS. 3 and 4.

Embodiment 5

Figure 3:
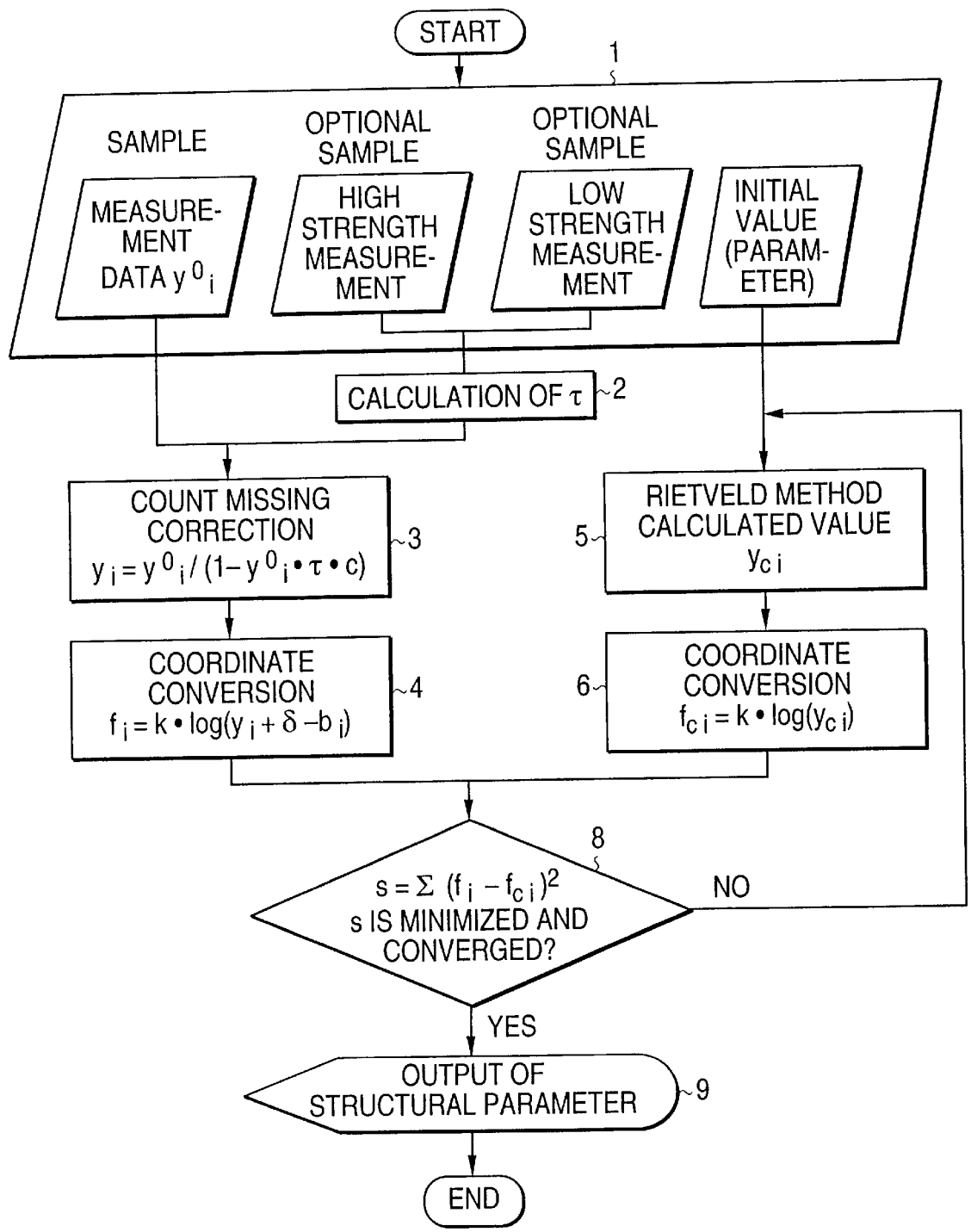
FIG. 3 is a diagram showing flow of an embodiment of the crystal structure parameter analyzing method according to the present invention.
Figure 4:
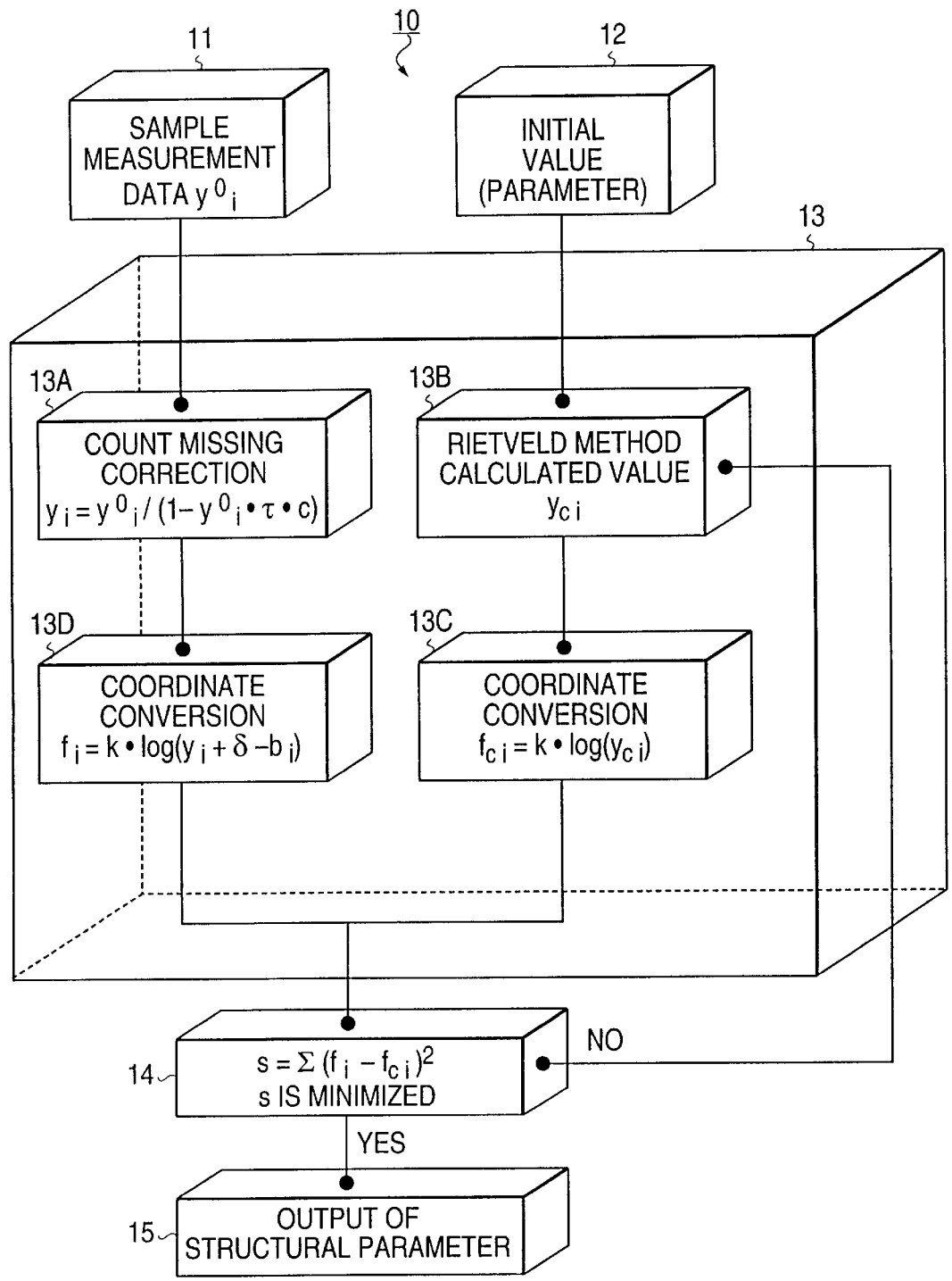
FIG. 4 is a diagram showing the structure of an embodiment of the crystal structure parameter analyzing apparatus according to the present invention.

In the crystal structure parameter analyzing method shown in FIG. 3, the weight calculation processing by Formula 8 in step 7 is omitted from the analyzing method shown in FIG. 1. Consequently, in step 8, using calculation of the residual square sum s by Formula 22 ($s=\Sigma W_i(f_i-f_i)^2$), to the logarithmic conversion value $f_i$ obtained in step 4 and the logarithmic conversion value $f_{ci}$ obtained in step 6, a determination is made as to whether or not the residual square sum s in Formula 22 is minimized and converged. For example, in a computer, when converged, step 9 is carried out. When not converged, an instruction is made to repeat the steps (5, 6, 8) after step 5. Other steps are the same as in FIG. 1. Even without using the weight matrix $w_i$ by Formula 3 as in the present embodiment, a determination is made as to whether or not the measured conversion value $f_i$ and the calculated conversion value $f_{ci}$ are sufficiently close to each other by determining whether or not the residual square sum s in Formula 22 is minimized and converged, and calculation procedure from the Rietveld method is repeated until the values are sufficiently close to each other, whereby the crystal structure can be analyzed with higher accuracy than the prior art, even though high resolution is not achieved as shown in FIG. 8.

$$s = \sum_{i=1}^{n} W_i(f_i - f_{ci})^2 \qquad (22)$$

Embodiment 6

A crystal structure parameter analyzing apparatus for calculating the crystal structure from a diffraction spectrum using the above-described crystal structure parameter analyzing method of FIG. 3 will be described with reference to FIG. 4 which shows the structure of the apparatus. In the crystal structure parameter analyzing apparatus shown in FIG. 4, the weight calculation unit 13E by Formula 3 is omitted from the analyzing apparatus shown in FIG. 2, consequently, in the determination unit 14, by determining whether or not the residual square sum s by Formula 22 is minimized and converged, a determination is made as to whether or not the measured value $f_i$ and the calculated value $f_{ci}$ after logarithmic conversion obtained by the logarithmic conversion unit 13D and 13C are sufficiently close to each other, when not sufficiently close to each other, an instruction is made again to the calculation unit 13 to recalculate by changing the crystal structure parameter, and when close to each other, an instruction is made to input the crystal structure parameter into the output unit 15. Other structure is the same as in FIG. 2. Even without using the weight $w_i$ by Formula 3 as in the present embodiment, a determination is made as to whether or not the measured value $f_i$ and the calculated value $f_{ci}$ are sufficiently close to each other by determining whether or not the residual square sum s in Formula 22 is minimized and converged, and calculation procedure of the calculated value $y_{ci}$ from the Rietveld method is repeated until the values are sufficiently close to each other, whereby the crystal structure can be analyzed with higher accuracy than the prior art.

In the above description, the calculation formula of Rietveld method suited to polycrystal structure analysis is used in the calculation of the calculated value $y_{ci}$. However, the present invention is not limited to this calculation formula, but various formulae for calculating the calculated value $y_{ci}$ from the crystal structure parameter can also be used such as those used in various single crystal structure analyzing methods and polycrystal structure analyzing methods including 4-axis diffraction method, pattern decomposition method, WPPD method, ab intio method, and the like. That is, the present invention can be applied to both polycrystal structure analysis and single crystal structure analysis, and the accuracy is improved over the prior art in either case.

Further, the present invention is not limited to crystal structure parameter analysis, but can also be applied to vibration analysis by Raman spectroscopy, surface state analysis by electron diffraction method, band state analysis by photoluminescence method and the like, and the accuracy of the structural parameter is improved over the prior art.

As described above, the present invention can be applied widely to crystal structure analyzing methods of all types of crystal materials with advantageous effects, whether polycrystal samples or single crystal samples, and whether Rietveld method or 4-axis diffraction method, or the like, and is useful in research and development of various functional and crystal structural materials such as ceramics, metal materials, and organic materials. Further, the present invention can also be applied to vibration analysis by Raman spectroscopy, surface state analysis by electron diffraction method, band state analysis by photoluminescence method and the like, to obtain advantageous effects.

Still further, with the present invention, the measure value vector and the calculated value are logarithmic converted, when obtaining the structural parameter of crystals by convergence calculation to determine the calculated value so that the residual square sum of these logarithmic conversion value vectors is minimized, effects of systematic error included in the measured value vectors can be corrected, thereby obtaining analytical results of generally higher accuracy over the prior art Rietveld method which considers only statistical variation.

Still further, when determining the residual square sum of the measured value vector F and logarithmic conversion value vector $F_c$, by multiplying the weighting $w_i$ calculated using these logarithmic conversion value vectors, effects of errors due to statistical variation can be corrected, thereby determining structural parameters of crystals of even higher accuracy over the prior art Rietveld method.

Moreover, as to the resolution, by introducing the non-diagonal term of the weight matrix W. The resolution is continuously improved in principle as far as the measuring time is allowed, and the structural parameters of crystal can be obtained with much higher accuracy over the prior art Rietveld method.

The invention being thus described, it will be obvious that the same may be varied in many ways. Such variations are not to be regarded as a departure from the spirit and scope of the invention, and all such modifications as would be obvious to one skilled in the art are intended to be included with the scope of the following claims.

What is claimed is:

1. A structural parameter analyzing apparatus comprising:
a structural parameter setting unit for setting a structural parameter;
a data input unit for inputting a measured value of a sample;
calculated value calculation means for determining a calculation value corresponding to the measured value according to the structural parameter from said structural parameter setting unit;
first logarithmic conversion means for making logarithmic conversion of the calculated value;
second logarithmic conversion means for logarithmic converting a value of the measured value subtracted by a background strength;
sum total calculation means for squaring a difference between the two logarithmic conversion values obtained by said first and second logarithmic conversion means to obtain a sum total s;
a determination unit for determining a minimum of a plurality of sum totals s obtained by said sum total calculation means by varying the structural parameter; and
an output unit for outputting a structural parameter of the minimum sum total.

2. The structural parameter analyzing apparatus as claimed in claim 1, further comprising correction means for correcting for count missing of a detector for obtaining the measured value, wherein said second logarithmic conversion means makes logarithmic conversion of a value of the measured value after count missing correction subtracted by the background strength.

3. The structural parameter analyzing apparatus as claimed in claim 1, wherein said second logarithmic conversion means subtracts the background strength from the measured value, adds a positive number of less than 1, and further makes logarithmic conversion.

4. The structural parameter analyzing apparatus as claimed in claim 3 comprising correction means for correcting for count missing of the detector for obtaining the measured value, wherein said second logarithmic conversion means makes logarithmic conversion of a value of the measured value after count missing correction subtracted by the background strength and after addition of a positive number of less than 1.

5. The structural parameter analyzing apparatus as claimed in claim 3, further including weight calculation means for obtaining a weight $w_i$ by Formula 1 from the two logarithmic conversion values obtained by said first and second logarithmic conversion means, said sum total calculation means squares a difference between the two logarithmic conversion values obtained by said first and second logarithmic conversion means and multiplies with the weight $w_i$ obtained by said weight calculation means to obtain a sum total calculated by $$s = \sum_{i=1}^{n} w_i \{k \cdot \log(y_i + \delta - b_i) - k \cdot \log(y_{ci})\}^2$$

$$w_i = \left[1 + \left\{(n-m) \cdot k^2 (y'_i + \delta - b_i)^{-2} (y_i + \delta) - (n-m)/n \cdot \sum_{i=1}^{n} k^2 (y_i + \delta - b_i)^{-2} (y_i + \delta)\right\} \Big/ \sum_{i=1}^{n} \{k \cdot \log(y_i + \delta - b_i) - k \cdot \log(y_{ci})\}^2\right]^{-1} n^{-1},$$

wherein i and j are numbers of measuring points, n is a total number of measuring points, m is a number of independent variables, k is a constant, $w_i$ is a weight, $y_i$ and $y_j$ are measured values, $\delta$ is a positive number of less than 1, $b_i$ and $b_j$ are background strengths, and $y_{ci}$ and $y_{cj}$ are calculated values.

6. The structural parameter analyzing apparatus as claimed in claim 5, wherein the number m of independent variables is set to zero.

7. The structural parameter analyzing apparatus as claimed in claim 5, comprising correction means for correcting for count missing of the detector for obtaining the measured value, wherein said second logarithmic conversion means makes logarithmic conversion of a value of the measured value after count missing correction subtracted by the background strength and after addition of a positive number of less than 1.

8. The structural parameter analyzing apparatus as claimed in claim 3 further including weight calculation means for obtaining a weight matrix W from vectors F an $F_c$ having two logarithmic conversion values obtained by said first and second logarithmic conversion means as matrix elements, wherein said sum total calculation means multiplies a transposition matrix $(F-F_c)^t$ of a difference between two logarithmic conversion value vectors obtained by said first and second logarithmic conversion means, by the weight matrix W obtained by said weight calculation means, and by a difference $(F-F_c)$ between two logarithmic conversion values obtained by said first and second logarithmic conversion means to obtain a sum total s, calculated by $$s = (F - F_c)^t W (F - F_c)$$

$$W = \left(\sum_{POI} + \sum_{SYS}\right)^{-1}$$

$$\sum_{SYS} = \left[(F - F_c)^t (F - F_c) - (n-m)/n \cdot \sum_{j=1}^{n} \{k^2 (y_j + \delta - b_j)^{-2} (y_j + \delta)\}\right] \Big/ n \cdot H^t H,$$

wherein s is a residual square sum, i and j are numbers of measuring points, $y_i$ is an i'th measured value after count missing correction, $y_{ci}$ is an i'th calculated value, k is a constant, n is a number of total measuring points, m is a number of independent variables, $\delta$ is a positive number of less than 1, $b_i$ is an i'th background strength, W is a weight matrix of n lines and n lows, F is a vector of n lines and 1 row having $f_i = k \cdot \log(y_i + \delta - b_i)$ as a matrix element, $F_c$ is a vector of n lines and 1 row having $f_{ci} = k \cdot \log(y_{ci})$ as a matrix element, $\Sigma_{POI}$ is a covariation matrix of n lines and n rows having $k^2 (y_i + \delta - b_i)^{-2} (y_i + \delta)$ as a diagonal element due to white noise (Poisson distribution), $\Sigma_{SYS}$ is a covariation matrix of n lines and n rows due to systematic error, H is a device function matrix (spread function matrix due to measuring device) of n lines and n rows, and $H_t$ is a transposition matrix of H.

9. The structural parameter analyzing apparatus as claimed in claim 8, comprising correction means for correcting for count missing of the detector for obtaining the measured value, wherein said second logarithmic conversion means makes logarithmic conversion of a value of the measured value after count missing correction subtracted by the background strength and after addition of a positive number of less than 1.

10. The structural parameter analyzing apparatus as claimed in claim 8, wherein the number m of independent variables is set to zero.

11. The structural parameter analyzing apparatus as claimed in claim 3, further includes weight calculation means which uses a variance $\sigma_{ir-1}^2$ obtained by actually measuring at each measuring point (point i) of data measured r times, to obtain the weight $w_i$ by $$r\sigma_{ir-1}^2 = \left\{\sum_{j=1}^{r} (y_i(j) - y_i/r^2)\right\} \Big/ (r-l) \times r$$

$$y_i = \sum_{j=1}^{r} y_i(j)$$

$$s = \sum_{i=1}^{n} w_i \{k \cdot \log(y_i + \delta - b_i) - k \cdot \log(y_{ci})\}^2$$

$$w_i = \left[1 + \left\{(n-m) \cdot k^2 (y'_i + \delta - b_i)^{-2} (r\sigma_{ir-1}^2) - (n-m)/n \cdot \sum_{j=1}^{n} k^2 (y_j + \delta - b_j)^{-2} (r\sigma_{jr-1}^2)\right\} \Big/ \sum_{j=1}^{n} \{k \cdot \log(y_i + \delta - b_j) - k \cdot \log(y_{cj})\}^2\right]^{-1} n^{-1},$$

wherein $y_i$ (r) is r'th measured value after count missing correction at point i, $y_i$ is a sum of measured values after count missing correction of r times at point i, i and j are numbers of measuring points, n is a total number of measuring points, m is a number of independent variables, k is a constant, $w_i$ is a weight, $\delta$ is a positive number of less than 1, $b_i$ and $b_j$ are background strengths, and $y_{ci}$ and $y_{cj}$ are calculated values.

12. The structural parameter analyzing apparatus as claimed in claim 11, comprising correction means for correcting for count missing of the detector for obtaining the measured value, wherein said second logarithmic conversion means makes logarithmic conversion of a value of the measured value after count missing correction subtracted by the background strength and after addition of a positive number of less than 1.

13. The structural parameter analyzing apparatus as claimed in claim 11, wherein the number m of independent variables is set to zero.

14. The structural parameter apparatus as claimed in claim 3, further including weight calculation means which uses a variance $\sigma_{ir-1}^2$ obtained by measuring at each measuring point (point i) of data measured r times, to obtain the weight matrix W $$r\sigma_{ir-1}^2 = \left\{\sum_{j=1}^{r}(y_i(j) - y_i/r)^2\right\} / (r-l) \times r$$

$$y_i = \sum_{j=1}^{r} y_i(j)$$

$$s = (F - F_c)^t W(F - F_c)$$

$$W = \left(\sum_{POI} + \sum_{SYS}\right)^{-1}$$

$$\sum_{SYS} = \left[(F - F_c)^t(F - F_c) - (n-m)/n \cdot \sum_{j=1}^{n}\{k^2(y_j + \delta - b_j)^{-2}(r\sigma_{jr-l}^2)\}\right]/n \cdot H^t H,$$

wherein $y_i(r)$ is an r'th measured value after count missing correction at point i, $y_i$ is a sum of measured values after count missing correction r times at point i, s is a residual square sum, i and j are number of measuring points, $y_{ci}$ is an i'th calculated value, k is a constant, n is a total number of measuring points, m is a number of independent variables, δ is a positive number of less than 1, $b_i$ is an i'th background strength, W is a weight matrix of n lines and n rows, F is a vector of n lines and 1 row having $f_i = k \cdot \log(y_i + \sigma - b_i)$ as a matrix element, $F_c$ is a vector of n lines and 1 row having $f_{ci} = k \cdot \log(y_{ci})$ as a matrix element, $\Sigma_{POI}$ is a covariation matrix of n lines and n rows having $(y_i + \delta - b_i)^{-2}(r\tau_{ir-1}^2)$ as a diagonal element due to white noise (Poisson distribution), $\Sigma_{SYS}$ is a covariation matrix of n lines and n rows due to systematic error, H is a device function matrix (spread function matrix due to measuring device) of n lines and n rows, and $H^t$ is a transposition matrix of H.

15. The structural parameter analyzing apparatus as claimed in claim 14, comprising correction means for correcting for count missing of the detector for obtaining the measured value, wherein said second logarithmic conversion means makes logarithmic conversion of a value of the measured value after count missing correction subtracted by the background strength and after addition of a positive number of less than 1.

16. The structural parameter analyzing apparatus as claimed in claim 14, wherein the number m of independent variables is set to zero.

17. The structural parameter analyzing apparatus as claimed in claim 3, said sum total being calculated by $$s = \sum_{i=1}^{n}\{k \cdot \log(y_i + \delta - b_i) - k \cdot \log(y_{ci})\}^2$$

wherein s is a sum total, i is a number of measuring point, n is a total number of measuring points, k is a constant, $y_i$ is a measured value, δ is a positive number of less than 1, $b_i$ is a background strength, and $y_{ci}$ is a calculated value.

18. The structural parameter analyzing apparatus as claimed in claim 17, comprising correction means for correcting for count missing of the detector for obtaining the measured value, wherein said second logarithmic conversion means makes logarithmic conversion of a value of the measured value after count missing correction subtracted by the background strength and after addition of a positive number of less than 1.

19. The structural parameter analyzing apparatus as claimed in claim 3, said sum total being calculated by $$s = \sum_{i=1}^{n}\{k \cdot \log(y_i + \delta - b_i) - k \cdot \log(y_{ci})\}^2 + g(y_i, y_{ci})$$

wherein s is a sum total, i is a number of measuring point, n is a total number of measuring points, k is a constant, $y_i$ is a measured value, δ is a positive number of less than 1, $b_i$ is a background strength, $y_{ci}$ is a calculated value, and $g(y_i, y_{ci})$ is an arbitrary function.

20. The structural parameter analyzing apparatus as claimed in claim 19, comprising correction means for correcting for count missing of the detector for obtaining the measured value, wherein said second logarithmic conversion means makes logarithmic conversion of a value of the measured value after count missing correction subtracted by the background strength and after addition of a positive number of less than 1.

21. The structural parameter analyzing apparatus as claimed in claim 3, said sum total being calculated by $$s = \sum_{i=1}^{n} w_i\{k \cdot \log(y_i + \delta - b_i) - k \cdot \log(y_{ci})\}^2$$

wherein s is a sum total, i is a number of measuring point, n is a total number of measuring points, k is a constant, $w_i$ is an arbitrary weight, $y_i$ is a measured value, δ is a positive number of less than 1, $b_i$ is a background strength, and $y_{ci}$ is a calculated value.

22. The structural parameter analyzing apparatus as claimed in claim 21, comprising correction means for correcting for count missing of the detector for obtaining the measured value, wherein said second logarithmic conversion means makes logarithmic conversion of a value of the measured value after count missing correction subtracted by the background strength and after addition of a positive number of less than 1.

23. The structural parameter analyzing apparatus as claimed in claim 3, said sum total being calculated by $$s = \sum_{i=1}^{n} w_i\{k \cdot \log(y_i + \delta - b_i) - k \cdot \log(y_{ci})\}^2 + g(y_i, y_{ci})$$

wherein s is a sum total, i is a number of measuring point, n is a total number of measuring points, k is a constant, $w_i$ is an arbitrary weight, $y_i$ is a measured value, δ is a positive number of less than 1, $b_i$ is a background strength, $y_{ci}$ is a calculated value, and $g(y_i, y_{ci})$ is an arbitrary function.

24. The structural parameter analyzing apparatus as claimed in claim 23, comprising correction means for correcting for count missing of the detector for obtaining the measured value, wherein said second logarithmic conversion means makes logarithmic conversion of a value of the measured value after count missing correction subtracted by the background strength and after addition of a positive number of less than 1.

25. The structural parameter analyzing apparatus as claimed in claim 3, said sum total being calculated by $$s=(F-F_c)^t W(F-F_c)$$

wherein s is a residual square sum, F is a vector of n lines and 1 row having $f_i = k \cdot \log(y_i + \delta - b_i)$ as a matrix element, $F_c$ is a vector of n lines and 1 row having $f_{ci} = k \cdot \log(y_{ci})$ as a matrix element, $(F-F_c)^t$ is a transposition matrix of $(F-F_c)$, W is a unit vector, i is a number of measuring point, $y_i$ is an i'th measured value after count missing correction, $y_{ci}$ is an i'th calculated value, k is a constant, n is a number of total measuring points, $\delta$ is a positive number of less than 1 and $b_i$ is an i'th background strength.

26. The structural parameter analyzing apparatus as claimed in claim 25, comprising correction means for correcting for count missing of the detector for obtaining the measured value, wherein said second logarithmic conversion means makes logarithmic conversion of a value of the measured value after count missing correction subtracted by the background strength and after addition of a positive number of less than 1.

27. The structural parameter analyzing apparatus as claimed in claim 3, said sum total being calculated by $$s=(F-F_c)^t W(F-F_c)+g(y_i,y_{ci})$$

wherein s is a residual square sum, F is a vector of n lines and 1 row having $f_i = k \cdot \log(y_i + \delta - b_i)$ as a matrix element, $F_c$ is a vector of n lines and 1 row having $f_{ci} = k \cdot \log(y_{ci})$ as a matrix element, $(F-F_c)^t$ is a transposition matrix of $(F-F_c)$, W is a unit vector, i is a number of measuring point, $y_i$ is an i'th measured value after count missing correction, $y_{ci}$ is an i'th calculated value, k is a constant, n is a number of total measuring points, $\delta$ is a positive number of less than 1, $b_i$ is an i'th background strength, and $g(y_i, y_{ci})$ is an arbitrary function.

28. The structural parameter analyzing apparatus as claimed in claim 27, comprising correction means for correcting for count missing of the detector for obtaining the measured value, wherein said second logarithmic conversion means makes logarithmic conversion of a value of the measured value after count missing correction subtracted by the background strength and after addition of a positive number of less than 1.

29. The structural parameter analyzing apparatus as claimed in claim 3, said sum total being calculated by $$s=(F-F_c)^t W(F-F_c)+g(y_i,y_{ci})$$

wherein s is a residual square sum, F is a vector of n lines and 1 row having $f_i = k \cdot \log(y_i + \delta - b_i)$ as a matrix element, $F_c$ is a vector of n lines and 1 row having $f_{ci} = k \cdot \log(y_{ci})$ as a matrix element, $(F-F_c)^t$ is a transposition matrix of $(F-F_c)$, W is a unit vector, i is a number of measuring point, $y_i$ is an i'th measured value after count missing correction, $y_{ci}$ is an i'th calculated value, k is a constant, n is a number of total measuring points, $\delta$ is a positive number of less than 1, $b_i$ is an i'th background strength, and $g(y_i, y_{ci})=-\log\{\det(W)\}$.

30. The structural parameter analyzing apparatus as claimed in claim 29, comprising correction means for correcting for count missing of the detector for obtaining the measured value, wherein said second logarithmic conversion means makes logarithmic conversion of a value of the measured value after count missing correction subtracted by the background strength and after addition of a positive number of less than 1.

31. The structural parameter analyzing apparatus as claimed in claim 3, said sum total being calculated by $$s=(F-F_c)^t W(F-F_c)$$

wherein s is a residual square sum, F is a vector of n lines and 1 row having $f_i = k \cdot \log(y_i + \delta - b_i)$ as a matrix element, $F_c$ is a vector of n lines and 1 row having $f_{ci} = k \cdot \log(y_{ci})$ as a matrix element, $(F-F_c)^t$ is a transposition matrix of $(F-F_c)$, W is an arbitrary matrix, i is a number of measuring point, $y_i$ is an i'th measured value after count missing correction, $y_{ci}$ is an i'th calculated value, k is a constant, n is a number of total measuring points, $\delta$ is a positive number of less than 1 and $b_i$ is an i'th background strength.

32. The structural parameter analyzing apparatus as claimed in claim 31, comprising correction means for correcting for count missing of the detector for obtaining the measured value, wherein said second logarithmic conversion means makes logarithmic conversion of a value of the measured value after count missing correction subtracted by the background strength and after addition of a positive number of less than 1.

33. The structural parameter analyzing apparatus as claimed in claim 3, said sum total being calculated by $$s=(F-F_c)^t W(F-F_c)+g(y_i,y_{ci})$$

wherein s is a residual square sum, F is a vector of n lines and 1 row having $f_i = k \cdot \log(y_i + \delta - b_i)$ as a matrix element, $F_c$ is a vector of n lines and 1 row having $f_{ci} = k \cdot \log(y_{ci})$ as a matrix element, $(F-F_c)^t$ is a transposition matrix of $(F-F_c)$, W is an arbitrary matrix, i is a number of measuring point, $y_i$ is an i'th measured value after count missing correction, $y_{ci}$ is an i'th calculated value, k is a constant, n is a number of total measuring points, $\delta$ is a positive number of less than 1, $b_i$ is an i'th background strength, and $g(y_i, y_{ci})$ is an arbitrary function.

34. The structural parameter analyzing apparatus as claimed in claim 33, comprising correction means for correcting for count missing of the detector for obtaining the measured value, wherein said second logarithmic conversion means makes logarithmic conversion of a value of the measured value after count missing correction subtracted by the background strength and after addition of a positive number of less than 1.

35. The structural parameter analyzing apparatus as claimed in claim 3, said sum total being calculated by $$s=(F-F_c)^t W(F-F_c)+g(y_i,y_{ci})$$

wherein s is a residual square sum, F is a vector of n lines and 1 row having $f_i = k \cdot \log(y_i + \delta - b_i)$ as a matrix element, $F_c$ is a vector of n lines and 1 row having $f_{ci} = k \cdot \log(y_{ci})$ as a matrix element, $(F-F_c)^t$ is a transposition matrix of $(F-F_c)$, W is an arbitrary matrix, i is a number of measuring point, $y_i$ is an i'th measured value after count missing correction, $y_{ci}$ is an i'th calculated value, k is a constant, n is a number of total measuring points, is a positive number of less than 1, $b_i$ is an i'th background strength, and $g(y_i, y_{ci})=-\log\{\det(W)\}$.

36. The structural parameter analyzing apparatus as claimed in claim 35, comprising correction means for correcting for count missing of the detector for obtaining the measured value, wherein said second logarithmic conversion means makes logarithmic conversion of a value of the measured value after count missing correction subtracted by the background strength and after addition of a positive number of less than 1.

37. A structural parameter analyzing apparatus comprising:
   an input unit for inputting a measured structural parameter of a sample;
   calculated value calculation means for calculating an expected structural parameter corresponding to the measured structural parameter;
   logarithmic conversion means for performing a first logarithmic conversion of the expected structural parameter and for performing a second logarithmic conversion of the measured structural parameter; and
   calculating means for minimizing the difference between the first and second logarithmic conversions to determine a final structural parameter.

38. The structural parameter analyzing apparatus according to claim 37, wherein the calculation means minimizes the difference between the first and second logarithmic conversions by calculating a squared difference value between the first and second logarithmic conversions.

39. The structural parameter analyzing apparatus according to claim 37, wherein the calculation means minimizes the difference between the first and second logarithmic conversions by modifying the expected structural parameter.

40. The structural parameter analyzing apparatus according to claim 37, wherein the calculated value calculation means corrects the effects of systematic errors included in the measured structural parameter.

41. A structural parameter analyzing method, comprising the steps of:
   inputting a measured structural parameter of a sample;
   calculating an expected structural parameter corresponding to the measured structural parameter;
   performing a first logarithmic conversion of the expected structural parameter;
   performing a second logarithmic conversion of the measured structural parameter; and
   minimizing the difference between the first and second logarithmic conversions to determine a final structural parameter.

42. The structural parameter analyzing method according to claim 41, wherein the minimizing step minimizes the difference between the first and second logarithmic conversions by calculating a squared difference value between the first and second logarithmic conversions.

43. The structural parameter analyzing method according to claim 41, wherein the minimizing step minimizes the difference between the first and second logarithmic conversions by modifying the expected structural parameter.

44. The structural parameter analyzing method according to claim 41, wherein the calculating step value includes correcting the effects of systematic errors included in the measured structural parameter.

45. A structural parameter analyzing method for determining a structure of a sample by using a measured value of the sample and an expected structural parameter, comprising:
   determining a calculated value corresponding to the measured value according to the expected structural parameter, and obtaining a first logarithmic conversion value by logarithmic conversion of the calculated value;
   obtaining a second logarithmic conversion value by logarithmic conversion of the measured value subtracted by a background strength; and
   changing the structural parameter until said first and second logarithmic conversion values are sufficiently close to each other, determining the structural parameter at the close logarithmic conversion values to be an analytical result.

46. The structural parameter analyzing method as claimed in claim 45, wherein said second logarithmic conversion value is determined by subtracting the background strength from the measured value, adding a positive number of less than 1, and making logarithmic conversion.

47. A structural parameter analyzing method for determining a structure of a sample by using a measured value of the sample and an expected structural parameter, comprising:
   determining a calculated value corresponding to the measured value according to the expected structural parameter, and obtaining a first logarithmic conversion value by logarithmic conversion of the calculated value;
   making count missing correction of a detector to the measured value, subtracting the background strength from the corrected measured value, adding a positive number of less than 1, and making logarithmic conversion to obtain a second logarithmic conversion value;
   determining a weighting $w_i$ from said first and second logarithmic conversion values;
   squaring a difference between the two logarithmic conversion values obtained by said first and second logarithmic conversion means values, and multiplying by the weighting $w_i$ to obtain a sum total s; and
   determining a minimum of a plurality of sum totals s obtained by changing the structural parameter, and determining the structural parameter of the minimum sum total to be an analytical result calculated by $$s = \sum_{i=1}^{n} w_i \{k \cdot \log(y_i + \delta - b_i) - k \cdot \log(y_{ci})\}^2$$

$$w_i = \left[1 + \left\{(n-m) \cdot k^2 (y'_i + \delta - b_i)^{-2}(y_i + \delta) - \right.\right.$$

$$(n-m)/n \cdot \sum_{j=1}^{n} k^2 (y_j + \delta - b_j)^{-2}(y_j + \delta)\right\} \Big/$$

$$\left.\sum_{j=1}^{n} \{k \cdot \log(y_i + \delta - b_j) - k \cdot \log(y_{cj})\}^2\right]^{-1} n^{-1},$$

wherein i and j are numbers of measuring points, n is a total number of measuring points, m is a number of independent variables, k is a constant, $w_i$ is a weighting, $y_i$ and $y_j$ are measured values, δ is a positive number of less than 1, $b_i$ and $b_j$ are background strengths, and $y_{ci}$ and $y_{cj}$ are calculated values.

48. The structural parameter analyzing method as claimed in claim 47, wherein the number m of independent variables is set to zero.

49. The structural parameter analyzing method as claimed in claim 47, wherein the step of determining the weight $w_i$ includes measuring a variance $\tau_{ir-1}^2$ at each measuring point (point i) for data measured r times to obtain the weight $w_i$ by $$r\sigma_{ir-1}^2 = \left\{\sum_{j=1}^{r}(y_i(j) - y_i/r)^2\right\} \Big/ (r-1) \times r$$

$$y_i = \sum_{j=1}^{r} y_i(j)$$

$$s = \sum_{i=1}^{n} w_i \{k \cdot \log(y_i + \delta - b_i) - k \cdot \log(y_{ci})\}^2$$

$$w_i = \left[1 + \left\{(n-m) \cdot k^2(y_i + \delta - b_i)^{-2}(r\sigma_{ir-1}^2) - (n-m)/n \cdot \sum_{j=1}^{n} k^2(y_j + \delta - b_j)^{-2}(r\sigma_{jr-1}^2)\right\} \Big/ \sum_{j=1}^{n} \{k \cdot \log(y_j + \delta - b_j) - k \cdot \log(y_{cj})\}^2\right]^{-1} n^{-1},$$

wherein $y_i(r)$ is an r'th measured value after count missing correction at point i, $y_i$ is a sum of measured values after count missing correction r times at point i, i and j are numbers of measuring points, n is a total number of measuring points, m is a number of independent variables, k is a constant, $w_i$ is a weight, δ is a positive number of less than 1, $b_i$ and $b_j$ are background strengths, and $y_{ci}$ and $y_{cj}$ are calculated values.

50. The structural parameter analyzing method as claimed in claim 49, wherein the number m of independent variables is set to zero.

51. The structural parameter analyzing method as claimed in claim 49, wherein the step of determining the weight matrix W includes measuring a variance $\tau_{ir-1}^2$ at each measuring point (point 1) for data measured r times to obtain $$r\sigma_{ir-1}^2 = \left\{\sum_{j=1}^{r}(y_i(j) - y_i/r)^2\right\} \Big/ (r-1) \times r$$

$$y_i = \sum_{j=1}^{r} y_i(j)$$

$$s = (F - F_c)^t W (F - F_c)$$

$$W = \left(\sum_{POI} + \sum_{SYS}\right)^{-1}$$

$$\sum_{SYS} = \left[(F - F_c)^t(F - F_c) - (n-m)/n \cdot \sum_{j=1}^{n}\{k^2(y_j + \delta - b_j)^{-2}(r\sigma_{jr-1}^2)\}\right] \Big/ n \cdot H^t H,$$

wherein $y_i(r)$ is an r'th measured value after count missing correction at point i, $y_i$ is a sum of measured values after count missing correction r times at point i, s is a residual square sum, i and j are number of measuring points, $y_{ci}$ is an i'th calculated value k is a constant, n is a total number of measuring points, m is a number of independent variables, δ is a positive number of less than 1, $b_i$ is an i'th background strength, W is a weight matrix of n lines and n rows, F is a vector of n lines and 1 row having $f_i = k \cdot \log(y_i + \sigma - b_i)$ as a matrix element, $F_c$ is a vector of n lines and 1 row having $f_{ci} = k \cdot \log(y_{ci})$ as a matrix element, $\Sigma_{POI}$ is a covariation matrix of n lines and n rows having $(y_i + \delta - b_i)^{-2}(r\sigma_{ir-1}^2)$ as a diagonal element due to white noise (Poisson distribution), $\Sigma_{SYS}$ is a covariation matrix of n lines and n rows due to systematic error, H is a device function matrix (spread function matrix due to measuring device) of n lines and n rows, and $H^t$ is a transposition matrix of H.

52. The structural parameter analyzing method as claimed in claim 51, wherein the number m of independent variables is set to zero.

53. A structural parameter analyzing method for determining a structure of a sample by using a measured value of the sample and an expected structural parameter, comprising:

determining a calculated value corresponding to the measured value according to the expected structural parameter, and making logarithmic conversion of the calculated value to obtain a vector $F_c$ having a first logarithmic conversion value as a matrix element;

making count missing correction of a detector to the measured value, subtracting the background strength from the corrected measured value, adding a positive number of less than 1, and making logarithmic conversion to obtain a second logarithmic conversion value vector F having the logarithmic conversion value as a matrix element;

determining a weighting matrix W from said first and second logarithmic conversion value vectors $F_c$ and F;

multiplying a transposition matrix $(F-F_c)^t$, by the weighting matrix W, and a different $(F-F_c)$ between said first and second logarithmic conversion value vectors to obtain a sum total s; and determining a minimum of a plurality of sum totals s obtained by changing the structural parameter, and determining the structural parameter of the minimum sum total to be an analytical result calculated by $$s = (F - F_c)^t W (F - F_c)$$

$$W = \left(\sum_{POI} + \sum_{SYS}\right)^{-1}$$

$$\sum_{SYS} = \left[(F - F_c)^t(F - F_c) - (n-m)/n \cdot \sum_{j=1}^{n}\{k^2(y_j + \delta - b_j)^{-2}(y_j + \delta)\}\right] \Big/ n \cdot H^t H,$$

wherein s is a residual square sum, i and j are numbers of measuring points, $y_i$ is an i'th measured value after count missing correction, $y_{ci}$ is an i'th calculated value, k is a constant, n is a number of total measuring points, m is a number of independent variables, δ is a positive number of less than 1, $b_i$ is an i'th background strength, W is a weighting matrix of n lines and n rows, F is a vector of n lines and 1 row having $f_i=k\cdot\log(y_i\delta-b_i)$ as a matrix element, $F_c$ is a vector of n lines and 1 row having $f_{ci}=k\cdot\log(y_{ci})$ as a matrix element, $\Sigma_{POI}$ is a covariation matrix of n lines and n rows having $k^2(y_i+\delta\times b_i)^{-2}(y_i+\delta)$ as a diagonal element due to white noise (Poisson distribution), $\Sigma_{SYS}$ is a covariation matrix of n lines and n rows due to systematic error, H is a device function matrix (spread function matrix due to measuring device) of n lines and n rows, and $H_t$ is a transportation matrix of H.

54. The structural parameter analyzing method as claimed in claim 53, wherein the number m of independent variables is set to zero.

55. A structural parameter analyzing method for determining a structure of a sample by using a measured value of the sample and an expected structural parameter, comprising:

determining a calculated value corresponding to the measured value according to the expected structural parameter, and obtaining a first logarithmic conversion value by logarithmic conversion of the calculated value;

making count missing correction of a detector to the measured value, subtracting the background strength from the corrected measured value, adding a positive number of less than 1, and making logarithmic conversion to obtain a second logarithmic conversion value;

squaring a difference between the two logarithmic conversion values obtained by said first and second logarithmic conversion means values to obtain a sum total s; and determining a minimum of a plurality of sum totals s obtained by changing the structural parameter, and determining the structural parameter of the minimum sum total to be an analytical result calculated by $$s = \sum_{i=1}^{n} \{k \cdot \log(y_i + \delta - b_i) - k \cdot \log(y_{ci})\}^2$$

wherein, i is a number of measuring point, n is a total number of measuring points, k is a constant, $y_i$ is a measured value, $\delta$ is a positive number of less than 1, $b_i$ is a background strength, and $y_{ci}$ is a calculated value.

56. A structural parameter analyzing method for determining a structure of a sample by using a measured value of the sample and an expected structural parameter, comprising:

determining a calculated value corresponding to the measured value according to the expected structural parameter, and obtaining a first logarithmic conversion value by logarithmic conversion of the calculated value;

making count missing correction of a detector to the measured value, subtracting the background strength from the corrected measured value, adding a positive number of less than 1, and making logarithmic conversion to obtain a second logarithmic conversion value;

squaring a difference between the two logarithmic conversion values obtained by said first and second logarithmic conversion means values to obtain a sum total s; and determining a minimum of a plurality of sum totals s obtained by changing the structural parameter, and determining the structural parameter of the minimum sum total to be an analytical result calculated by $$s = \sum_{i=1}^{n} \{k \cdot \log(y_i + \delta - b_i) - k \cdot \log(y_{ci})\}^2 + g(y_i, y_{ci})$$

wherein, i is a number of measuring point, n is a total number of measuring points, k is a constant, $y_i$ is a measured value, $\delta$ is a positive number of less than 1, $b_i$ is a background strength, $y_{ci}$ is a calculated value, and $g(y_i, y_{ci})$ is an arbitrary function.

57. A structural parameter analyzing method for determining a structure of a sample by using a measured value of the sample and an expected structural parameter, comprising:

determining a calculated value corresponding to the measured value according to the expected structural parameter, and obtaining a first logarithmic conversion value by logarithmic conversion of the calculated value;

making count missing correction of a detector to the measured value, subtracting the background strength from the corrected measured value, adding a positive number of less than 1, and making logarithmic conversion to obtain a second logarithmic conversion value;

squaring a difference between the two logarithmic conversion values obtained by said first and second logarithmic conversion means values to obtain a sum total s; and determining a minimum of a plurality of sum totals s obtained by changing the structural parameter, and determining the structural parameter of the minimum sum total to be an analytical result calculated by $$s = \sum_{i=1}^{n} w_i \{k \cdot \log(y_i + \delta - b_i) - k \cdot \log(y_{ci})\}^2$$

wherein, i is a number of measuring point, n is a total number of measuring points, k is a constant, $w_i$ is an arbitrary weight, $y_i$ is a measured value, $\delta$ is a positive number of less than 1, $b_i$ is a background strength, and $y_{ci}$ is a calculated value.

58. A structural parameter analyzing method for determining a structure of a sample by using a measured value of the sample and an expected structural parameter, comprising:

determining a calculated value corresponding to the measured value according to the expected structural parameter, and obtaining a first logarithmic conversion value by logarithmic conversion of the calculated value;

making count missing correction of a detector to the measured value, subtracting the background strength from the corrected measured value, adding a positive number of less than 1, and making logarithmic conversion to obtain a second logarithmic conversion value;

squaring a difference between the two logarithmic conversion values obtained by said first and second logarithmic conversion means values to obtain a sum total s; and determining a minimum of a plurality of sum totals s obtained by changing the structural parameter, and determining the structural parameter of the minimum sum total to be an analytical result calculated by $$s = \sum_{i=1}^{n} w_i \{k \cdot \log(y_i + \delta - b_i) - k \cdot \log(y_{ci})\}^2 + g(y_i, y_{ci})$$

wherein, i is a number of measuring point, n is a total number of measuring points, k is a constant, $w_i$ is an arbitrary weight, $y_i$ is a measured value, $\delta$ is a positive number of less than 1, $b_i$ is a background strength, $y_{ci}$ is a calculated value, and $g(y_i, y_{ci})$ is an arbitrary function.

59. A structural parameter analyzing method for determining a structure of a sample by using a measured value of the sample and an expected structural parameter, comprising:

determining a calculated value corresponding to the measured value according to the expected structural parameter, and making logarithmic conversion of the calculated value to obtain a vector $F_c$ having a first logarithmic conversion value as a matrix element;

making count missing correction of a detector to the measured value, subtracting the background strength from the corrected measured value, adding a positive number of less than 1, and making logarithmic conversion to obtain a second logarithmic conversion value vector F having the logarithmic conversion value as a matrix element;

multiplying a transportation matrix $(F-F_c)^t$, by a difference $(F-F_c)$ between said first and second logarithmic conversion value vectors to obtain a sum total s; and determining a minimum of a plurality of sum totals s obtained by changing the structural parameter, and determining the structural parameter of the minimum sum total to be an analytical result, calculated by $$s=(F-F_c)^t W(F-F_c)$$

wherein s is a residual square sum, F is a vector of n lines and 1 row having $f_i = k \cdot \log(y_i + \delta - b_i)$ as a matrix element, $F_c$ is a vector of n lines and 1 row having $f_{ci} = k \cdot \log(y_{ci})$ as a matrix element, $(F-F_c)^t$ is a transposition matrix of $(F-F_c)$, W is a unit vector, i is a number of measuring point, $y_i$ is an i'th measured value after count missing correction, $y_{ci}$ is an i'th calculated value, k is a constant, n is a number of total measuring points, $\delta$ is a positive number of less than 1 and $b_i$ is an i'th background strength.

60. A structural parameter analyzing method for determining a structure of a sample by using a measured value of the sample and an expected structural parameter, comprising:

determining a calculated value corresponding to the measured value according to the expected structural parameter, and making logarithmic conversion of the calculated value to obtain a vector $F_c$ having a first logarithmic conversion value as a matrix element;

making count missing correction of a detector to the measured value, subtracting the background strength from the corrected measured value, adding a positive number of less than 1, and making logarithmic conversion to obtain a second logarithmic conversion value vector F having the logarithmic conversion value as a matrix element;

multiplying a transportation matrix $(F-F_c)^t$, by a difference $(F-F_c)$ between said first and second logarithmic conversion value vectors to obtain a sum total s; and determining a minimum of a plurality of sum totals s obtained by changing the structural parameter, and determining the structural parameter of the minimum sum total to be an analytical result, calculated by $$s=(F-F_c)^t W(F-F_c)+g(y_i,y_{ci})$$

wherein s is a residual square sum, F is a vector of n lines and 1 row having $f_i = k \cdot \log(y_i + \delta - b_i)$ as a matrix element, $F_c$ is a vector of n lines and 1 row having $f_{ci} = k \cdot \log(y_{ci})$ as a matrix element, $(F-F_c)^t$ is a transposition matrix of $(F-F_c)$, W is a unit vector, i is a number of measuring point, $y_i$ is an i'th measured value after count missing correction, $y_{ci}$ is an i'th calculated value, k is a constant, n is a number of total measuring points, $\delta$ is a positive number of less than 1, $b_i$ is an i'th background strength, and $g(y_i, y_{ci})$ is an arbitrary function.

61. A structural parameter analyzing method for determining a structure of a sample by using a measured value of the sample and an expected structural parameter, comprising:

determining a calculated value corresponding to the measured value according to the expected structural parameter, and making logarithmic conversion of the calculated value to obtain a vector $F_c$ having a first logarithmic conversion value as a matrix element;

making count missing correction of a detector to the measured value, subtracting the background strength from the corrected measured value, adding a positive number of less than 1, and making logarithmic conversion to obtain a second logarithmic conversion value vector F having the logarithmic conversion value as a matrix element;

multiplying a transportation matrix $(F-F_c)^t$, by a difference $(F-F_c)$ between said first and second logarithmic conversion value vectors to obtain a sum total s; and determining a minimum of a plurality of sum totals s obtained by changing the structural parameter, and determining the structural parameter of the minimum sum total to be an analytical result, calculated by $$s=(F-F_c)^t W(F-F_c)+g(y_i,y_{ci})$$

wherein s is a residual square sum, F is a vector of n lines and 1 row having $f_i = k \cdot \log(y_i + \delta - b_i)$ as a matrix element, $F_c$ is a vector of n lines and 1 row having $f_{ci} = k \cdot \log(y_{ci})$ as a matrix element, $(F-F_c)^t$ is a transposition matrix of $(F-F_c)$, W is a unit vector, i is a number of measuring point, $y_i$ is an i'th measured value after count missing correction, $y_{ci}$ is an i'th calculated value, k is a constant, n is a number of total measuring points, $\delta$ is a positive number of less than 1, $b_i$ is an i'th background strength, and $g(y_i,y_{ci})$ is $=-\log\{\det(W)\}$.

62. A structural parameter analyzing method for determining a structure of a sample by using a measured value of the sample and an expected structural parameter, comprising:

determining a calculated value corresponding to the measured value according to the expected structural parameter, and making logarithmic conversion of the calculated value to obtain a vector $F_c$ having a first logarithmic conversion value as a matrix element;

making count missing correction of a detector to the measured value, subtracting the background strength from the corrected measured value, adding a positive number of less than 1, and making logarithmic conversion to obtain a second logarithmic conversion value vector F having the logarithmic conversion value as a matrix element;

multiplying a transportation matrix $(F-F_c)^t$, by an arbitrary weight matrix W, and a difference $(F-F_c)$ between said first and second logarithmic conversion value vectors to obtain a sum total s; and determining a minimum of a plurality of sum totals s obtained by changing the structural parameter, and determining the structural parameter of the minimum sum total to be an analytical result, calculated by $$s=(F-F_c)^t W(F-F_c)$$

wherein s is a residual square sum, F is a vector of n lines and 1 row having $f_i=k \cdot \log(y_i+\delta-b_i)$ as a matrix element, $F_c$ is a vector of n lines and 1 row having $f_{ci}=k \cdot \log(y_{ci})$ as a matrix element, $(F-F_c)^t$ is a transposition matrix of $(F-F_c)$, W is an arbitrary weight matrix, i is a number of measuring point, $y_i$ is an i'th measured value after count missing correction, $y_{ci}$ is an i'th calculated value, k is a constant, n is a number of total measuring points, $\delta$ is a positive number of less than 1 and $b_i$ is an i'th background strength.

63. A structural parameter analyzing method for determining a structure of a sample by using a measured value of the sample and an expected structural parameter, comprising:

determining a calculated value corresponding to the measured value according to the expected structural parameter, and making logarithmic conversion of the calculated value to obtain a vector $F_c$ having a first logarithmic conversion value as a matrix element;

making count missing correction of a detector to the measured value, subtracting the background strength from the corrected measured value, adding a positive number of less than 1, and making logarithmic conversion to obtain a second logarithmic conversion value vector F having the logarithmic conversion value as a matrix element;

multiplying a transportation matrix $(F-F_c)^t$, by an arbitrary weight matrix W, and a difference $(F-F_c)$ between said first and second logarithmic conversion value vectors to obtain a sum total s; and determining a minimum of a plurality of sum totals s obtained by changing the structural parameter, and determining the structural parameter of the minimum sum total to be an analytical result, calculated by $$s=(F-F_c)^t W(F-F_c)+g(y_i,y_{ci})$$

wherein s is a residual square sum, F is a vector of n lines and 1 row having $f_i=k \cdot \log(y_i+\delta-b_i)$ as a matrix element, $F_c$ is a vector of n lines and 1 row having $f_{ci}=k \cdot \log(y_{ci})$ as a matrix element, $(F-F_c)^t$ is a transposition matrix of $(F-F_c)$, W is an arbitrary weight matrix, i is a number of measuring point, $y_i$ is an i'th measured value after count missing correction, $y_{ci}$ is an i'th calculated value, k is a constant, n is a number of total measuring points, $\delta$ is a positive number of less than 1, $b_i$ is an i'th background strength, and $g(y_i, y_{ci})$ is an arbitrary function.

64. A structural parameter analyzing method for determining a structure of a sample by using a measured value of the sample and an expected structural parameter, comprising:

determining a calculated value corresponding to the measured value according to the expected structural parameter, and making logarithmic conversion of the calculated value to obtain a vector $F_c$ having a first logarithmic conversion value as a matrix element;

making count missing correction of a detector to the measured value, subtracting the background strength from the corrected measured value, adding a positive number of less than 1, and making logarithmic conversion to obtain a second logarithmic conversion value vector F having the logarithmic conversion value as a matrix element;

multiplying a transportation matrix $(F-F_c)^t$, by an arbitrary weight matrix W, and a difference $(F-F_c)$ between said first and second logarithmic conversion value vectors to obtain a sum total s; and determining a minimum of a plurality of sum totals s obtained by changing the structural parameter, and determining the structural parameter of the minimum sum total to be an analytical result, calculated by $$s=(F-F_c)^t W(F-F_c)+g(y_i,y_{ci})$$

wherein s is a residual square sum, F is a vector of n lines and 1 row having $f_i=k \cdot \log(y_i+\delta-b_i)$ as a matrix element, $F_c$ is a vector of n lines and 1 row having $f_{ci}=k \cdot \log(y_{ci})$ as a matrix element, $(F-F_c)^t$ is a transposition matrix of $(F-F_c)$, W is an arbitrary weight matrix, i is a number of measuring point, $y_i$ is an i'th measured value after count missing correction, $y_{ci}$ is an i'th calculated value, k is a constant, n is a number of total measuring points, $\delta$ is a positive number of less than 1, $b_i$ is an i'th background strength, and $g(y_i,y_{ci})$ is $=-\log\{\det(W)\}$.

* * * * *